United States Patent [19]
Judd et al.

[11] Patent Number: 5,910,112
[45] Date of Patent: Jun. 8, 1999

[54] $^{23}$NA AND $^{39}$K IMAGING OF THE HEART

[75] Inventors: Robert M. Judd, Wheeling; Todd B. Parrish, Chicago, both of Ill.

[73] Assignee: Northwestern University, Evanston, Ill.

[21] Appl. No.: 08/827,809

[22] Filed: Apr. 11, 1997

Related U.S. Application Data

[60] Provisional application No. 60/030,638, Nov. 8, 1996.

[51] Int. Cl.$^6$ ...................................................... A61B 5/055
[52] U.S. Cl. ........................................... 600/410; 324/318
[58] Field of Search ..................................... 324/318, 322, 324/309, 307; 600/410

[56] References Cited

U.S. PATENT DOCUMENTS

| | | | |
|---|---|---|---|
| 4,779,618 | 10/1988 | Winkler | 600/410 |
| 5,168,227 | 12/1992 | Foo et al. | 324/309 |
| 5,200,345 | 4/1993 | Young | 600/410 |
| 5,303,705 | 4/1994 | Nenov | 600/410 |

*Primary Examiner*—Ruth S. Smith
*Attorney, Agent, or Firm*—Leydig, Voit & Mayer, Ltd

[57] ABSTRACT

Methods for increasing the efficiency of $^{23}$Na and $^{39}$K imaging of biological tissue are provided. For maximum efficiency, the receiver bandwidth is set equal to or less than the quantity $N_{ro}/T^*2$. Methods for assessing cardiac tissue viability using $^{23}$Na imaging are also provided.

18 Claims, 12 Drawing Sheets

$^{23}$NA AND $^{39}$K IMAGING OF THE HEART

CROSS-REFERENCE TO RELATED APPLICATION

This application is related to and claims priority of United States Provisional Patent Application Serial Number 60/030,638, filed on Nov. 8, 1996.

Funds used to support the studies disclosed herein were provided in part by the United States Government (NIH-NHLBI R29-HL53411). The United States government, therefore, may have certain rights in the invention.

TECHNICAL FIELD OF THE INVENTION

The field of this invention is magnetic imaging of biological tissue. More particularly, this invention relates to $^{23}$Na and $^{39}$K magnetic resonance imaging of the heart and the use of such imaging to assess cardiac cell viability.

BACKGROUND OF THE INVENTION

In many clinical situations, it is critical to determine whether a given tissue is viable following an ischemic episode. For example, in cardiology the decision to intervene by thrombolytics, percutaneous transluminal coronary angioplasty (PTCA), or coronary artery bypass grafting (CABG) is made largely on the assumption that the affected myocardium is viable and therefore will benefit from the procedure (Bonow, R. O. Identification of viable myocardium. *Circulation* 94:2674–2680, (1996), Hendel, R. C. and Bonow, Ro. O. Disparity in coronary perfusion and regional wall motion: effect on clinical assessment of viability. *Coron. Art Disease* 4(6):512–520, (1993)). Similarly, treatment of stroke patients is strongly influenced by available information regarding tissue viability Shimizu, T., Naritomi, H., Kuriyama, Y. and Sawada, T. Sequential changes if sodium magnetic resonance images after cerebral hemorrhage. *Neuroradiology* 34(4):301–304 (1992)). Thus, one of the most important issues regarding the management of patients with cardiovascular disease is knowledge of the location and extent of injured but viable tissue.

Extensive clinical experience has demonstrated that one of the best approaches for determining viability is to test for normal cell membrane function (Bonow, R. O. Identification of viable myocardium. *Circulation* 94:2674–2680, (1996), Hendel, R. C. and Bonow, R. O. Disparity in coronary perfusion and regional wall motion: effect on clinical assessment of viability. *Coron. Art Disease* 4(6):512–520, (1993)), i.e. to test for continued function of the $Na^+$-$K^+$ pump. The most abundant natural isotopes of Na and K, $^{23}$Na and $^{39}$K, can be detected by magnetic resonance. In principle, it should be possible to use $^{23}$Na and $^{39}$K MRI to non-invasively examine cell membrane function and therefore viability. Specifically, we have recently shown in an animal model that $^{23}$Na image intensity is approximately 100% higher in non-viable compared to viable regions following reperfused myocardial infarction (Kim, R. J., Lima, J. A. C., Chen, E-L., Reeder, S. B., Klocke, F. J., Zerhouni, E. A. and Judd, R. M. Fast 23Na magnetic resonance imaging of acute reperfused myocardial infarction:potential to assess myocardial viability. *Circulation* in press:(1997)). Unfortunately, however, the in vivo $^{23}$Na and $^{39}$K MR signals are very small. The MR sensitivities for $^{23}$Na and $^{39}$K are only 9.2 and 0.051% of the $^1$H MR sensitivity and that the in vivo concentrations of these nuclei are approximately 1,000 times lower than the in vivo water proton concentration. The combination of these factors results in $^{23}$Na and $^{39}$K MR signals which are approximately 22,000 ($1/4.63\times10^{-5}$) and 2.1 million ($1/4.73\times10^{-7}$) times smaller than the standard $^1$H signal, respectively.

Despite the small MR signal, several groups have succeeded in producing in vivo $^{23}$Na images of humans Shimizu, T., Naritomi, H., Kuriyama, Y. and Sawada, T. Sequential changes if sodium magnetic resonance images after cerebral hemorrhage. *Neuroradiology* 34(4):301–304, (1992))-, Ra, J. B., Hilal, S. K., Oh, C. H. and Mun, I. K. In vivo magnetic resonance imaging of sodium in the human body. *Magn. Reson. Med.* 7:11–22, (1988), Granot, J. Sodium imaging by gradient reversal. *J. Magn. Reson.* 68:575–581, (1986); Granot, J. Sodium imaging of human body organs and extremities in vivo. *Radiology* 167:547–550, (1988), Katz, J. and Cannon, P. J. Use of sodium-23 for cardiac magnetic resonance imaging and spectroscopy. In: *Cardiac imaging*, edited by Marcus, M. L., Skorton, D. L., Schelbert, H. R. and Wold, G. L. Philadelphia: W. B. Suanders Co., 1991, p. 828–840; Perman, W. H., Turski, P. A., Houston, L. W., Glover, G. H. and Hayes, C. E. Methodology of in vivo humans sodium imaging at 1.5 T. *Radiology* 160:811–820, (1986), Hilal, S. K., Maudsley, A. A., Ra, J. B., Simon, H. E., Roschmann, P., Wittekoek, S., Cho, Z. H. and Mun, S. K. In vivo NMR imaging of sodium-23 in the human head. *J. Comp. Assist. Tomog.* 9(1):1–7, (1985), Winkler, S. S. Sodium-23 magnetic resonance brain imaging. *Neuroradiology* 32:416–420, (1990)). However, most of these groups have not attempted to apply recently-developed high speed gradient-echo imaging techniques to the $^{23}$Na or $^{39}$K nuclei. One reason for the lack of high-speed imaging studies of $^{23}$Na may be that many groups are interested in quantifying intracellular $Na^+$ concentrations, for which long TR's to ensure full relaxation are desirable. In addition, high-speed imaging of nuclei like $^{23}$Na and $^{39}$K is very demanding on gradient hardware due to the low gyromagnetic ratios. Recent advances in gradient technology, however, may make this issue less significant.

Because the $T_1$ and $T_2$ relaxation times of $^{23}$Na and $^{39}$K are much shorter than those of $^1$H [data taken from (Wolf, G. L. Contrast agents for cardiac MRI. In: *Cardiac imaging*, edited by Marcus, M. L., Skorton, D. L., Schelbert, H. R. and Wold, G. L. Philadelphia: W. B. Saunders Co., 1991, p. 794–810), (Kim, R. J., Lima, J. A. C., Chen, E-L., Reeder, S. B., Klocke, F. J., Zerhouni, E. A. and Judd, R. M. Fast 23Na magnetic resonance imaging of acute reperfused myocardial infarction:potential to assess myocardial viability. *Circulation* in press:(1997), and (Burstein, D., Litt, H. I. and Fossel, E. T. NMR characteristics of "visible" intracellular myocardial potassium in perfused rat hearts. *Magn. Reson. Med.* 9:66–78, (1989)) for $^1$H, $^{23}$Na, and $^{39}$K, respectively], it is unlikely that direct application of fast imaging concepts derived from experience with proton imaging would result in optimal imaging parameters for $^{23}$Na and $^{39}$K imaging. There continues to be a need in the art, therefore, for improved methods for $^{23}$Na and $^{39}$K imaging.

The present invention provides numerically simulated various imaging strategies to maximize $^{23}$Na and $^{39}$K signal acquisition per unit time to understand the effect of the short relaxation parameters on the data collection. Then using the simulation results as a guide, in vivo 3D $^{23}$Na images of the human heart were acquired in 15 minutes on a modified 1.5 T clinical scanner. The results show that the application of high-speed gradient-echo imaging techniques combined with recent advances in gradient technology make $^{23}$Na imaging of the human heart practical.

BRIEF SUMMARY OF THE INVENTION

Numerical simulations of high-speed imaging sequences were developed and used to maximize $^{23}$Na and $^{39}$K image SNR per unit time within the constraints of existing gradient hardware. The simulation demonstrated that decreasing receiver bandwidth at the expense of echo time (TE) results in a substantial increase in $^{23}$Na and $^{39}$K image SNR/time despite the short $T_2$ and $T_2^*$ of these nuclei. Referenced to the available $^1$H signal on existing 1.5 T scanners, the simulation suggested that it should be possible to acquire 3D $^{23}$Na images of the human heart with 7×7×7 mm resolution and $^{39}$K images with 26×26×26 mm resolution in 30 min. Experimentally in humans at 1.5 T, 3D $^{23}$Na images of the heart were acquired in 15 min with 6×6×12 mm resolution and SNRs of 11 and 7 in the left ventricular cavity and myocardium, respectively, which is very similar to the predicted result. The results demonstrate that by choosing imaging pulse sequence parameters which fully exploit the short relaxation times of $^{23}$Na and $^{39}$K, potassium MRI is improved but remains impractical whereas sodium MRI improves to the point where $^{23}$Na imaging of the human heart may be clinically feasible on existing 1.5 T scanners.

In accordance with such simulations, the present invention provides a method of increasing the efficiency of 23Na magnetic resonance imaging of biological tissue, the process including the step of acquiring images with a receiver bandwidth equal to or less than $R(N_{ro}/T^*_{2Na})$ where R is an integer from 1 to about 5. Preferably, R is from about 1 to about 3, and more preferably R is from about 1 to about 2.

In one embodiment, the bandwidth is from about 500 Hz to about 10,000 Hz. More preferably, the bandwidth is from about 1,000 Hz to about 5,000 Hz, from about 2,500 Hz to about 5,000 Hz and, most preferably, from about 2,500 Hz to about 3,000 Hz.

The 23Na images are acquired using a 1.5 T, 3.0 T or a 4.0 T scanner. The images are preferably acquired in from about 15 to about 60 minutes, from about 30 to about 45 minutes and, most preferably, in about 30 minutes. The biological tissue can be located in a living organism. Preferably the biological tissue is a human heart.

In another aspect, a process of this invention increases the efficiency of 39K magnetic resonance imaging of biological tissue. The process includes the step of acquiring images with a receiver bandwidth equal or less and $R(N_{ro}/T^*_{2K})$, where R is an integer from 1 to about 5. The bandwidth is from about 1,000 Hz to about 30,000 Hz and, preferably, is about 8,000 Hz.

The present invention further provides a process of identifying regional areas of myocardial damage in vivo. The process includes the step of imaging the heart in vivo using $^{23}$Na magnetic resonance imaging wherein regions of relative high image $^{23}$Na intensity indicate the damaged regions. The damaged regions of the myocardium are nonviable tissue resulting from any pathological condition such as ischemia. In addition, recently developed rapid gradient-echo techniques used for proton imaging have been applied to the sodium nucleus to explore methods to reduce $^{23}$Na imaging time to a level which would allow $^{23}$Na imaging to become a practical experimental and clinical tool.

Where the heart is imaged using $^{23}$Na imaging, that imaging is accomplished using a) an imaging time of from about 3 minutes to about 20 minutes; b) about 16 phase encodes per cardiac cycle; c) an echo time of from about 2.5 milliseconds to about 6.5 milliseconds; d) a repetition time of from about 8 milliseconds to about 20 milliseconds; e) a signal averaging of from about 2090 to about 300; f) a voxel size of about 1.0–1.5×2.0–3.0×4.0–8.0 millimeters.

Preferably, the imaging time is from about 6 to about 15 minutes, more preferably from about 8 to about 12 minutes and, most preferably about 10 or 11 minutes. The echo time is preferably from about 3.5 milliseconds to about 5.5 milliseconds and, more preferably about 4.5 milliseconds. The repetition time is preferably from about 10 milliseconds to about 15 milliseconds and, more preferably about 13 milliseconds. The signal averaging is preferably from about 225 to about 275 and, more preferably about 256. A preferred voxel size is about 1.25×2.5×6 millimeters.

The present disclosure establishes the relationship of regional changes in sodium image intensity to myocardial viability without the need to distinguish between intra- and extracellular Na$^+$. Regional image intensity, both in isolated hearts and in vivo, correlated with myocardial viability determined by TTC (triphenyltetrazolium chloride) staining techniques, regional differences in sodium content measured using, $^{23}$Na MR spectroscopy, and regional differences in sodium $T_1$ and $T_2$ relaxation times.

The physiologic and technical feasibility of using $^{23}$Na MRI to examine myocardial viability has been established. Eighteen rabbits underwent in situ coronary artery occlusion and reperfusion. $^{23}$Na images were obtains in these rabbits, normal rabbits, and normal dogs. In infarcted, reperfused regions $^{23}$Na image intensity was greater than in viable regions (isolated hearts: 42±5%, $p<0.02$, in vivo: 95±6%, $p<0.001$). Data from $^{23}$Na MR spectroscopy showed a similar pattern ($p<0.001$). Following acute infarction with reperfusion, a regional increase in $^{23}$Na MR image intensity is associated with nonviable myocardium. Fast gradient-echo imaging techniques can reduce $^{23}$Na imaging time to a few minutes.

DETAILED DESCRIPTION OF THE INVENTION

Figure 1A:
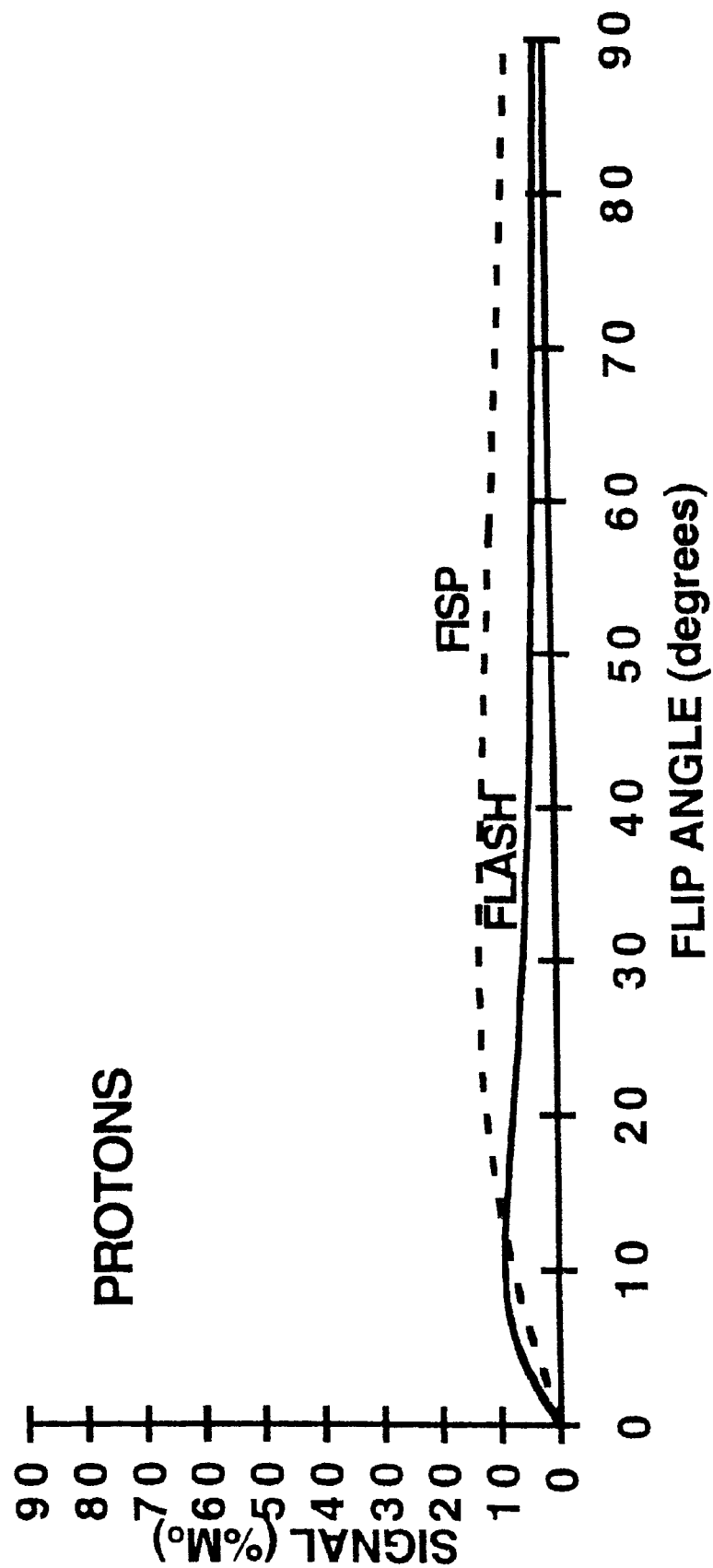
FIG. 1 shows MR signal from a FLASH sequence vs. flip angle at a fixed TR=15 ms, TE=0, given relaxation parameters in Table 2. Panel (a) (top): protons, Panel (b) (middle): sodium, Panel (c) (bottom): potassium. Fast gradient-echo pulse sequences collect a greater percentage of the available MR signal for sodium and potassium compared to protons due to the short $T_1$ of sodium and potassium.

Taking the sensitivity, abundance and concentration into account, the signal deficits of $^{23}$Na and $^{39}$K are about 22,000 and 2.1 million, respectively, compared to the $^1$H MR signal (Table 1, below).

TABLE 1

In vivo magnetic resonance sensitivities of $^1$H, $^{23}$Na, and $^{39}$K

| Nucleus | % Abundance | Relative Sensitivity | In vivo Concentration | In vivo signal |
|---|---|---|---|---|
| $^1$H | 99.99 | 1.000000 | 100,000 | 1 |
| $^{23}$Na | 100.00 | 0.092500 | 50 | 4.63E-05 |
| $^{39}$k | 93.10 | 0.000508 | 100 | 4.73E-07 |

For $^{23}$Na and $^{39}$K imaging to be practical in humans, therefore, it is necessary to increase the signals by these amounts. As a numerical example, consider standard $^1$H imaging of the human heart. Using state-of-the-art hardware, it is possible to acquire a $^1$H image with 2×3×10 mm resolution in a single heartbeat, a technique typically used in conventional cardiac MRI. The design considerations set forth herein outline the method needed to acquire a sodium or potassium image with nearly identical SNR as the single heartbeat $^1$H image. For comparison purposes, the unit proton SNR is defined as that of a proton image with 2×3×10 mm resolution acquired in 1 sec with a receiver bandwidth of 100,000 Hz. In a typical 1.5 T clinical scanner with these parameters, the proton image SNR in the myocardium was 11.

Two approaches to increasing $^{23}$Na and $^{39}$K signal are to increase voxel size and lengthen imaging time Taking $^{23}$Na imaging as an example, increasing the size of the voxel from 2×3×10 mm to 6×6×12 mm would increase signal by a factor of 7. In addition, by increasing imaging time to thirty minutes an additional factor of 42 could be realized ($\sqrt{(30 min * 60 sec/min)}$). Although combining these two approaches would increase $^{23}$Na SNR by a factor of 294 (=7*42), this is still far from the necessary 22,000.

An additional gain in $^{23}$Na SNR can be realized by employing fast imaging pulse sequences which exploit the fast T$_1$ of $^{23}$Na, such as high-speed coherent (FISP, or GRASS) and incoherent (FLASH, or SPGR) gradient echo (GRE) sequences run with a very short TR. Furthermore, by employing short TRs, fast 3D imaging has significant advantages over a comparable 2D sequence for at least two reasons. First, a shorter echo time can be realized because the RF excitation is not slice-selective. Second, because $^{23}$Na (and $^{39}$K) imaging requires significant signal averaging, it is more time efficient to encode a third spatial dimension (Ra, J. B., Hilal, S. K., Oh, C. H. and Mun, I. K. In vivo magnetic resonance imaging of sodium in the human body. *Magn. Reson. Med.* 7:11–22, (1988), Wehrli, F. Fast-scan magnetic resonance: principles and applications. *Magn. Reson. Q.* 6:165–236, (1990)). The entire heart can be imaged in the same time as a 2D slice for a constant SNR.

In order to explore which type of sequence yielded the greatest increase in $^{23}$Na SNR, the steady state MR signal for each sequence using the T$_1$, T$_2$, and T$_2$* values given in Table 2, below, for $^1$H, $^{23}$Na, and $^{39}$K were plotted.

TABLE 2

Gyromagnetic Ratios and Relaxation Times for $^1$H, $^{23}$Na, and $^{39}$K

| Nucleus | Gyromagnetic Ratio ( ) [MHz/T] | T1 [ms] | T2 [ms] | T2* [ms] |
|---|---|---|---|---|
| $^1$H | 42.5 | 870 | 60 | 25 |
| $^{23}$Na | 11.2 | 35 | 30 | 25 |
| $^{39}$K | 1.98 | 10 | 8 | 8 |

Figure 1B:
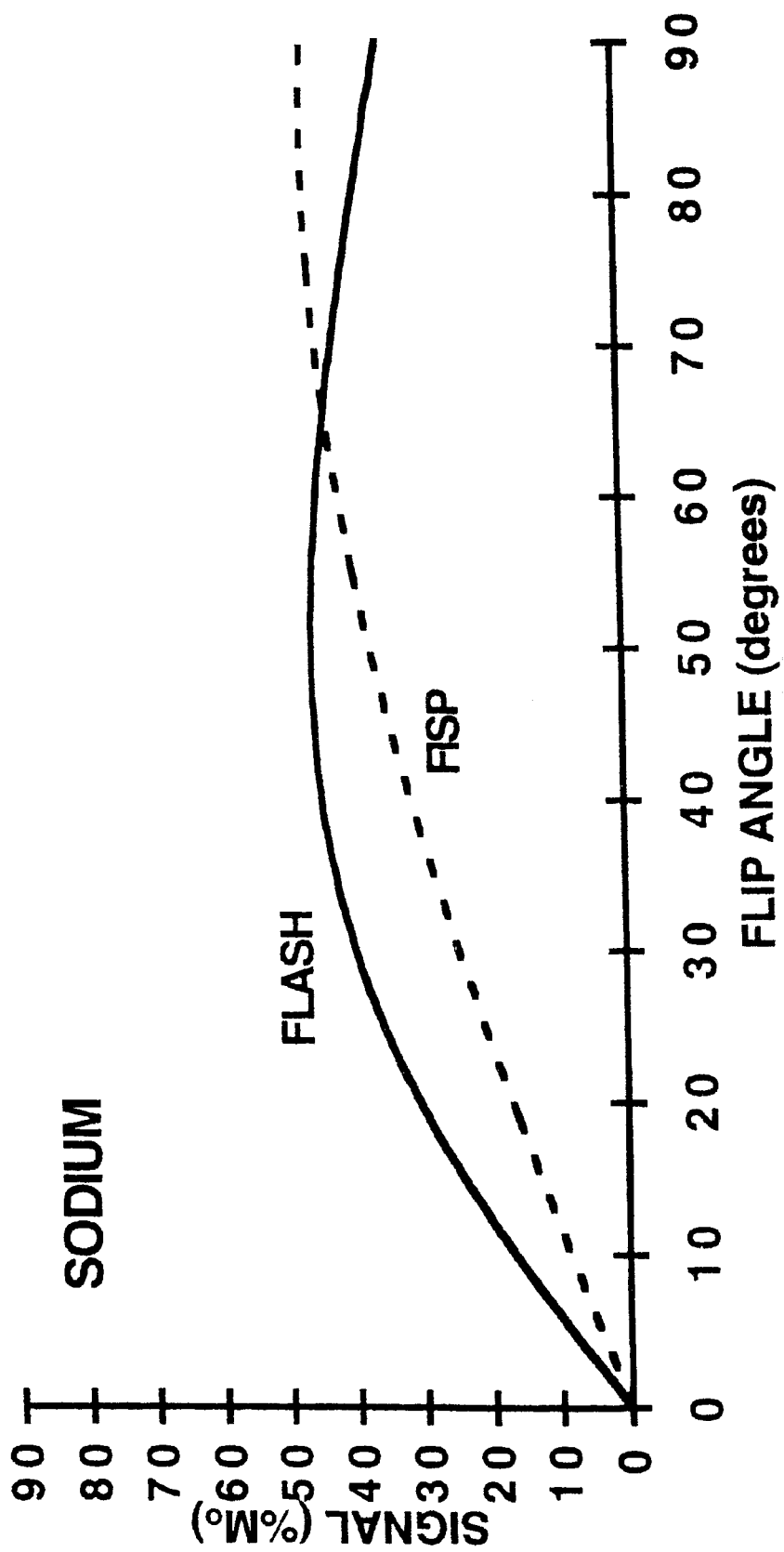
Figure 1C:
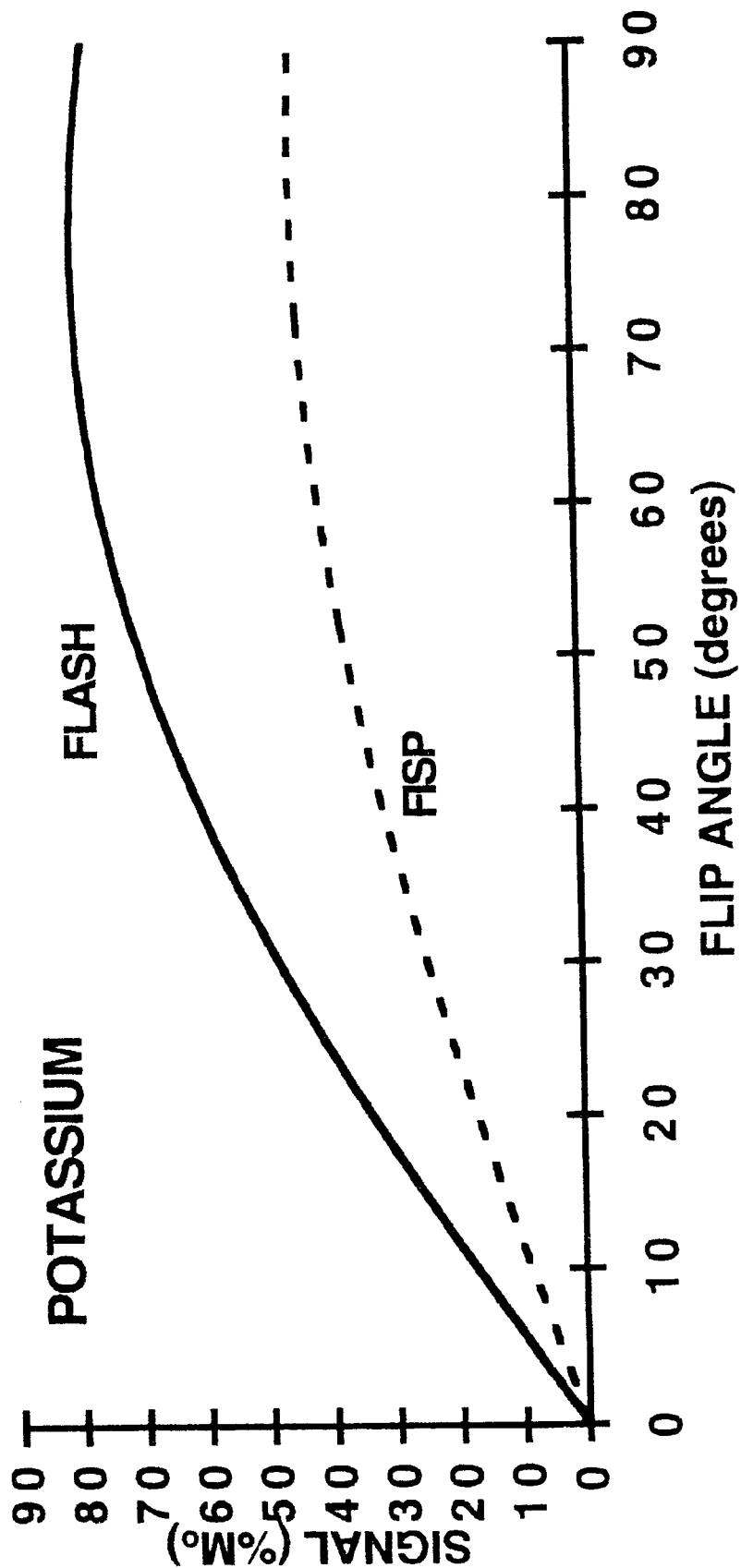

FIG. 1 shows signal for FISP and FLASH sequences using a TR of 15 ms. As expected in the case of $^1$H imaging (FIG. 1a), the FISP sequence had slightly more signal available. For $^{23}$Na imaging (FIG. 1b) there is no real difference between the peak magnitude of the FISP or FLASH signal. Contrary to proton-based imaging theory, the FLASH sequence is optimal for $^{39}$K (FIG. 1c).

The major advantage of using GRE imaging is that both the $^{23}$Na and $^{39}$K curves realize a much higher signal level compared to protons (50% vs. 8% of M$_0$ for $^{23}$Na and 80% vs. 8% of M$_0$ for $^{39}$K compared to $^1$H, respectively). Therefore, choosing the optimal sequence type for $^{23}$Na imaging increases the signal compared to protons by an additional factor of 6. When combined with larger voxels and longer imaging time, the $^{23}$Na signal from fast gradient echo imaging is now increased by 1,764 (=294*6).

Finally, choosing the optimal receiver bandwidth for $^{23}$Na (and $^{39}$K) imaging should likely yield an additional increase in signal. Although decreasing bandwidth generally increases SNR by reducing noise, the optimal choice of bandwidth for $^{23}$Na and $^{39}$K is unclear because decreasing bandwidth will result in a longer TE, which will decrease signal due to the short $T_2$ and $T_2^*$ of $^{23}$Na and $^{39}$K. In addition, the TR will increase and may affect SNR/time. For example, consider the plot in FIG. 2 which shows image SNR per unit time for a FLASH sequence as a function of TR with TE=0. As TR decreases, SNR/time reaches a plateau at or near the $T_1$ of each nucleus. One can calculate that for 6×6×12 mm voxels and state-of-the-art gradients (25 mT/m), one could achieve a TE of 1.3 ms and a TR of 3.1 ms for $^{23}$Na imaging. However, from FIG. 2 increasing the TR to almost 30 ms results in no penalty in the SNR/time (for TE=0). Therefore, neglecting $T_2^*$ losses for the moment, decreasing receiver bandwidth from 100,000 (Unit Proton SNR) to 2,500 for $^{23}$Na imaging might increase $^{23}$Na signal by as much as 6-fold (=√(100,000/2,500)). Consequently, the combined effects of increasing voxel size, increasing imaging time, using a fast 3D imaging sequence, and optimizing receiver bandwidth will likely increase the $^{23}$Na signal by 10,584 (=1,764*6), i.e. increase the $^{23}$Na signal to within a factor of two of the Unit Proton SNR. Analogous arguments suggest that the $^{39}$K signal would also approximate the Unit Proton SNR but would require larger voxels.

Choosing the imaging parameters that maximize SNR/time is difficult without full numerical simulation because changing a single parameter such as bandwidth directly affects other parameters such as TE, TR, and the optimal flip angle. The above considerations, however, make it likely that $^{23}$Na and $^{39}$K imaging is possible. Therefore, fast imaging pulse sequences for $^{23}$Na and $^{39}$K were numerically tested to determine the additional SNR/time which might be made available by application of high-speed imaging techniques.

Pulse Sequence Simulations

To determine the specific 3D GRE pulse sequence parameters which optimized $^{23}$Na and $^{39}$K image SNR per unit time, standard 3D FISP and FLASH pulse sequences were numerically simulated. The equations used in the simulations (Wehrli, F. Fast-scan magnetic resonance: principles and applications. *Magn. Reson. Q.* 6:165–236, (1990), Vlaardingerbroek, M. T. and den Boer, J. A. *Magnetic Resonance Imaging*, Berlin:Springer-Verlag, 1996) are given below.

The 3D FISP and FLASH sequences were simulated as follows. First, the variables $G_{max}$, SR, γ, PW, $N_{ro}$, $N_{pe}$, $N_{part}$, and $N_{el}$ were taken from Tables 2 and 3. For a given bandwidth (BW), the dwell time ($t_{dwell}$) was calculated as:

$$t_{dwell} = \frac{1}{BW}$$

the readout time ($t_{ro}$) was calculated as:

$$t_{ro} = N_{ro} \cdot t_{dwell}$$

and the amplitude of the readout gradient ($G_{ro}$) was calculated as:

$$G_{ro} = \frac{1}{\gamma \cdot t_{dwell} \cdot FOV}$$

Next, the number of points by which the echo was offset ($N_{eo}$) was calculated based on the number of points from the beginning of the readout window to the echo (echo location, $N_{el}$, from Table 3):

$$N_{eo} = \frac{N_{ro}}{2} - N_{el}$$

The echo offset was also calculated as a percent of the readout window ($\%_{eo}$):

$$\%_{eo} = \frac{N_{ro} - 2 \cdot N_{eo}}{2 \cdot N_{ro}}$$

Next, the time required for the readout dephaser ($t_{rd}$), phrase enclode ($t_{pe}$) and slice enclode ($t_s$) gradients were calculated assuming the gradients are run at maximum:

$$t_{rd} = \frac{G_{ro}}{G_{max}} \cdot \left( \%_{eo} \cdot t_{ro} + \frac{G_{ro}}{2 \cdot SR} \right)$$

$$t_{pe} = \frac{G_{ro} \cdot N_{pe}}{2 \cdot G_{max} \cdot N_{ro}} \cdot \left( t_{ro} + \frac{G_{ro}}{SR} \right)$$

$$t_s = \frac{N_{part}}{\gamma \cdot G_{max} \cdot FOV}$$

From these times, the actual encoding time, $t_e$, was taken as the maximum of $t_{rd}$, $t_{pe}$, $t_s$. Note that gradient duty cycle was not considered because our gradient system is capable of 100% duty. The echo time (TE) and repetition time (TR) were calculated as:

$$TE = \frac{PW}{2} + t_e + \frac{G_{ro}}{SR} + \%_{eo} \cdot t_{ro}$$

$$TR = PW + 2 \cdot t_e + \frac{2 \cdot G_{ro}}{SR} + t_{ro}$$

Next, the TE and TR values were combined with the Ernst angle (from Equation 4) and used with either Equation 2 (FLASH) or Equation 3 (FISP) to calculate the MR signal per TR ($S_{FLASH}$ or $S_{FISP}$). Finally, SNR/time was calculated using Equation 1. This process was repeated for bandwidths varying from 500 to 100,000 Hz to determine the bandwidth which maximized SNR/time for $^{23}$Na and $^{39}$K imaging.

Input parameters to the simulation were: gyromagnetic ratio and relaxation times for each nuclei, resolution, maximum gradient strength, maximum slew rate, and RF pulse width.

The simulation required an estimate of $T_2^*$, which depends on many factors such as geometry, field, etc. The $T_2^*$ can be estimated for $^{23}$Na and $^{39}$K by assuming a $T_2^*$ for $^1$H of 25 msec, which is typical on standard 1.5 T systems. Based on this assumption, an estimated magnetic field inhomogeneity, ΔB, from the equation $1/T_2^* = 1/T_2 + \gamma \Delta B$, can be calculated. Given the estimated ΔB, $T_2^*$ for $^{23}$Na and $^{39}$K were then calculated from their γ and $T_2$ values and the results are given in Table 2, above.

Because the pulse sequence timing is a strong function of gradient performance and resolution, specific imaging parameters given in Table 3, below, as typical of human heart imaging on a clinical scanner (1.5 T Siemens Vision) were used.

TABLE 3

Pulse sequence parameters used to simulate $^{23}$Na and $^{39}$K imaging

| Nucleus | $^{23}$Na | $^{39}$K |
|---|---|---|
| Maximum Gradient ($G_{max}$) [mT/m] | 25 | 25 |
| Slew Rate (SR) [(mT/m)/ms] | 25 | 25 |
| RF Pulse Width (PW) [μs] | 500 | 500 |
| Number Readout Samples ($N_{ro}$) | 64 | 64 |
| Echo Location ($N_e$) [Sample Number] | 12 | 12 |
| Number Phase Encoding Steps ($N_{pe}$) | 32 | 32 |
| Number Slice Encoding Steps ($N_{part}$) | 32 | 32 |

Given the parameters in Tables 2 and 3, the simulation calculated the minimum TE and TR for each pulse sequence type within the constraints of the gradient hardware. Once TE and TR were known, SNR per unit time was calculated according to Equation [1], below:

$$\frac{SNR}{unit\,time} = S \cdot \frac{1}{\sqrt{TR}} \cdot \frac{1}{\sqrt{bandwidth}} \quad [1]$$

where S is the percent of the fully relaxed magnetization (%$M_0$) sampled per RF pulse. For the case where transverse magnetization was spoiled (FLASH or SPGR) (Wehrli, F. Fast-scan magnetic resonance: principles and applications. *Magn. Reson. Q.* 6:165–236, (1990), Vlaardingerbroek, M. T. and den Boer, J. A. *Magnetic Resonance Imaging,* Berlin:Springer-Verlag, 1996), S was calculated from the Equation [2], below:

$$S_{FLASH} = \frac{M_0(1-e^{-TR/T_1})\sin\alpha}{1-e^{-TR/T_1}\cos\alpha} e^{-TE/T_2^*} \quad [2]$$

For the case where transverse magnetization was refocussed by rewinding the phase and slice encode gradients (FISP or GRASS), S was determined by Equation [3], below (Wehrli, F. Fast-scan magnetic resonance: principles and applications. *Magn. Reson. Q.* 6:165–236, (1990), Vlaardingerbroek, M. T. and den Boer, J. A. *Magnetic Resonance Imaging,* Berlin:Springer-Verlag, 1996):

$$S_{FISP} = \frac{M_0 \sin\alpha}{(1+T_1/T_2+(1-T_1/T_2)\cos\alpha)} e^{-TE/T_2^*} \quad [3]$$

For the case of spoiled transverse magnetization, the flip angle (a) was taken as the Ernst angle according to Equation [4], below:

$$\alpha_{ERNST} = \cos^{-1}\left(\frac{TR}{T_1}\right) \quad [4]$$

For the case of refocussed transverse magnetization, the optimum flip angle was determined numerically by maximizing S as defined in Equation [3], above.

Although it is known that noise decreases with decreasing bandwidth, lower bandwidth also increases TE which can result in significant loss of signal for $^{23}$Na and $^{39}$K, due to their short $T_2$ and $T_2^*$. The simulation was, therefore, designed to adjust bandwidth until an optimum SNR/t was found. However, as bandwidth is decreased at some point, the bandwidth per pixel will exceed the line width, $1/T_2^*$, resulting in blurring between pixels and a loss of spatial resolution. Bandwidth was constrained by the Equation [5], below:

$$Bandwidth > N_{ro}/T_2^* \quad [5]$$

where $N_{ro}$ is the number of readout samples.

Figure 3:
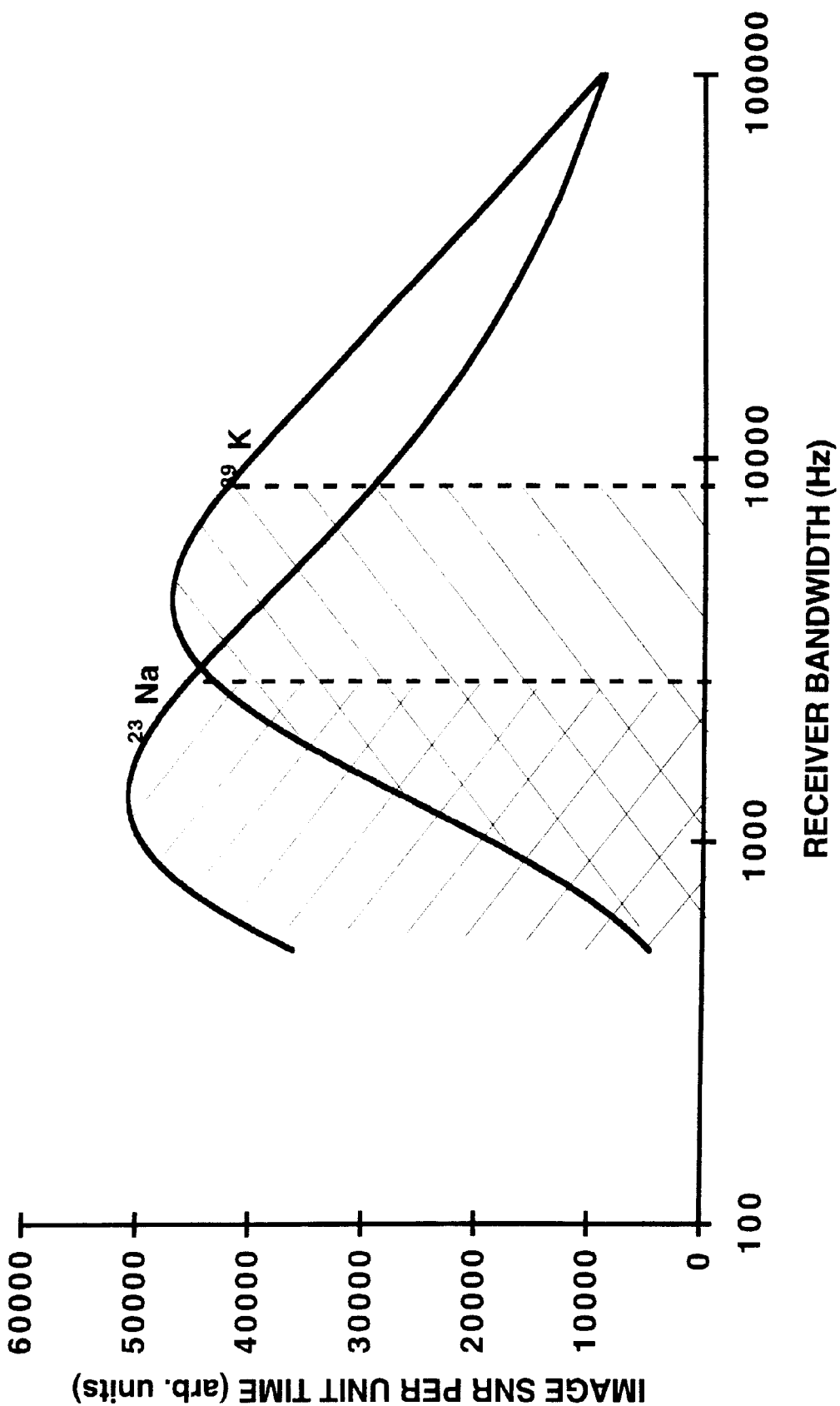
FIG. 3 shows image SNR per unit time vs. bandwidth for $^{23}$Na and $^{39}$K. For each nuclei and each value of bandwidth, TR, TE, and flip angle are changing according to the simulation. Shaded areas denote regions in which image blurring will occur as the bandwidth per pixel becomes less than $1/T_2^*$. The simulation suggests that blurring will occur before optimal image SNR per unit time can be achieved for both $^{23}$Na and $^{39}$K. NOTE: a bandwidth of 10,000 Hz is equivalent to ±5,000 Hz.

FIG. 3 shows the simulated effect of receiver bandwidth on optimized image SNR/time for $^{23}$Na and $^{39}$K using a voxel size of 6×6×6 mm for $^{23}$Na and 12×12×12 mm for $^{39}$K. Note that for each nucleus in FIG. 3, TE, TR and flip angle vary with bandwidth according to the simulation. From FIG. 3, for both nuclei SNR/time reaches a maximum value at bandwidths between 1,000 and 10,000 Hz. As previously noted, however, image spatial resolution will suffer if the bandwidth is decreased to a point where the bandwidth per pixel is less than the line width of the FID (i.e. when bandwidth<$N_{ro}/T_2^*$). For both nuclei, the bandwidth for which SNR/time was maximized was limited by this constraint. The exact location of these constraints for sodium and potassium are shown in FIG. 3. Specifically, it was found that the optimal bandwidths were 2,560 and 8,000 Hz for $^{23}$Na and $^{39}$K, respectively, corresponding to dwell times of 390 and 125 μsec. The important finding demonstrated by the results of FIG. 3 is that for the parameters in Tables 2 and 3, the optimal SNR/time without loss of spatial resolution for both nuclei will occur when bandwidth is set equal to $N_{ro}/T_2^*$. At those bandwidths, the optimal TR's were 26 and 10 ms for $^{23}$Na and $^{39}$K, respectively, and the optimal TE's were 5.2 and 2.4 ms, respectively.

Figure 2:
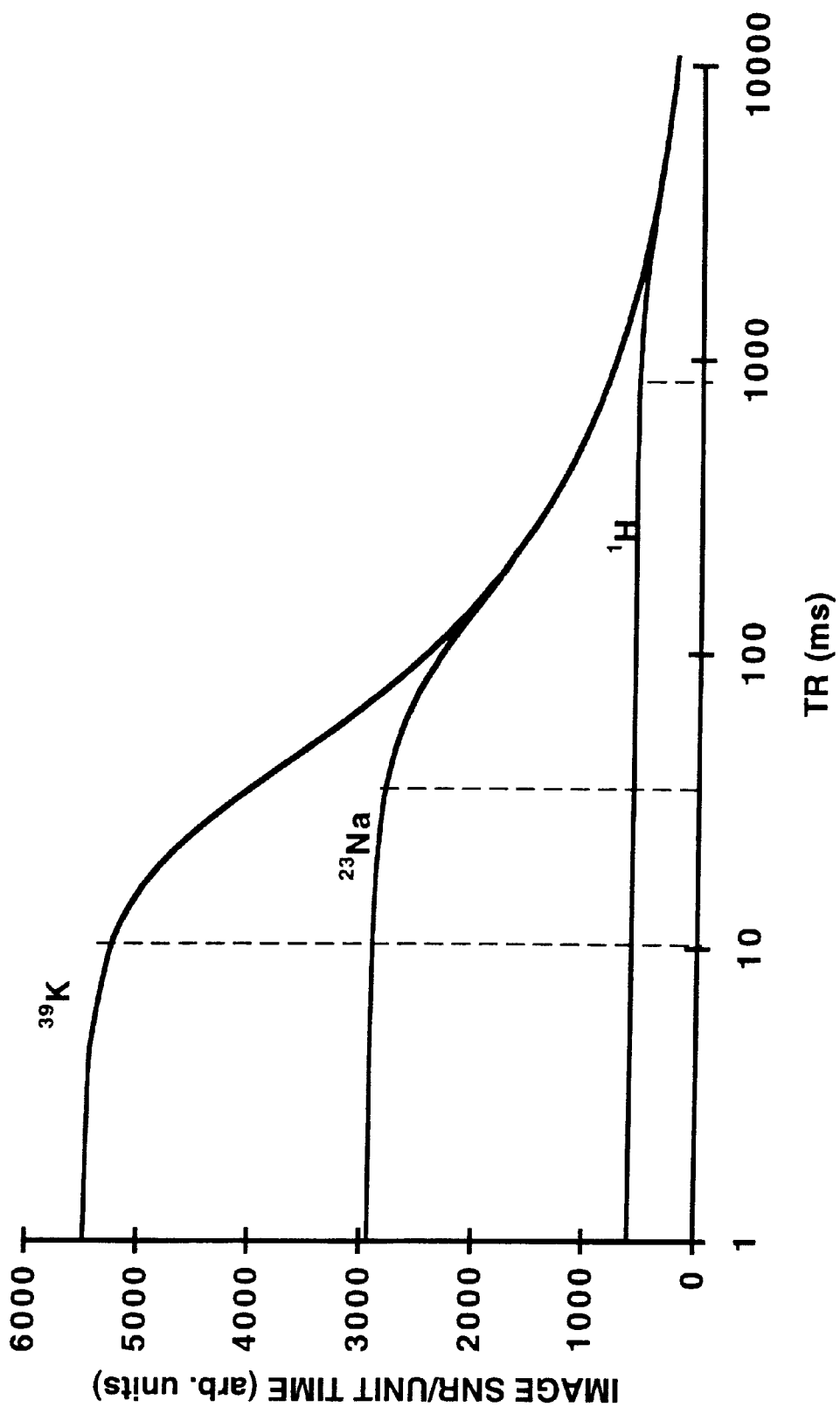
FIG. 2 shows image SNR per unit time vs. TR with TE=0. The dotted lines correspond to the $T_1$ of each nucleus. Although existing gradient hardware is typically capable of TRs less than 10 ms for $^{23}$Na and $^{39}$K, the time efficiency of imaging these nuclei is not improved as TR is decreased below $T_1$ suggesting that acquiring at maximum gradient amplitude might not achieve the optimal SNR/t. See text for details.

It is interesting to note that for both $^{23}$Na and $^{39}$K the maximum SNR/time does not occur at the shortest possible TE (i.e. all gradients run at maximum) despite the short $T_2$ and $T_2^*$ of these nuclei (Table 2). To understand this result, consider the $^{23}$Na results in FIG. 3 for bandwidths of 100,000 and 2,560 Hz. At a bandwidth of 100,000 Hz, the simulation calculated that the gradients could achieve a TE=1.3 ms and TR=3.1 ms and at 2,560 Hz the simulation calculated a TE=5.2 and TR=26. Because both TRs are shorter than $^{23}$Na T, (Table 2), the flip angle (24° at 100,000 and 61° at 2,560) was adjusted by the simulation according to the Ernst equation (Equation 4) to maintain a constant SNR/time with regard to $T_1$ relaxation (FIG. 2). Consequently, the only parameters affecting SNR/time in this example are $T_2^*$ decay and bandwidth. Due to the longer echo time, the signal decreases by a factor of $(e^{-1.3/25})/(e^{-5.2/25})$=1.17. However, due to the lower bandwidth the noise is reduced by a factor of $(1/\sqrt{2,560})/(1/\sqrt{100,000})$=6.25. Thus an unexpected result is that bandwidth is more important than a short echo time for the parameters used in this simulation.

Figure 4:
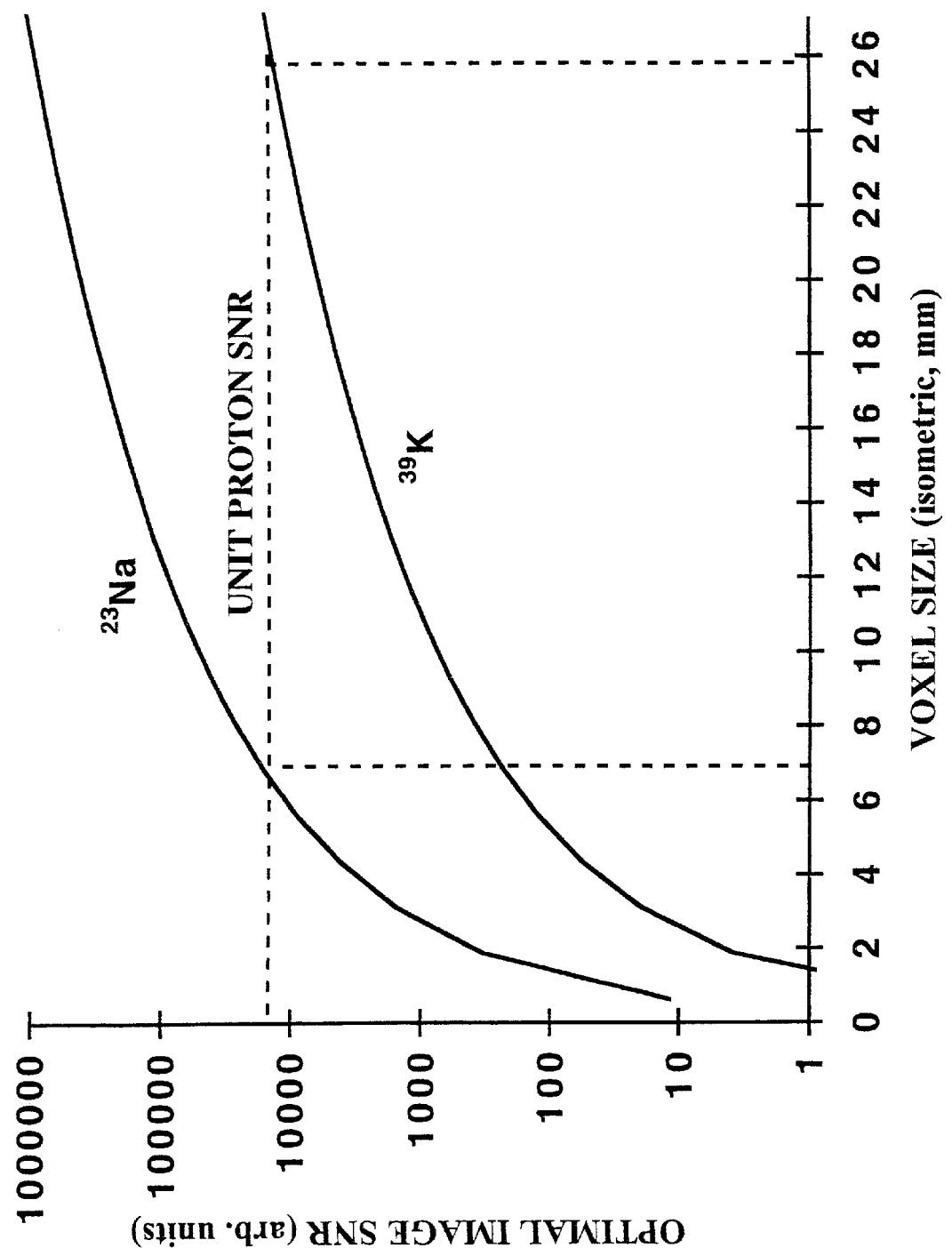
FIG. 4 shows optimized $^{23}$Na and $^{39}$K image SNR for human heart parameters on a clinical 1.5 T scanner assuming a fixed imaging time of 30 min as a function of isometric voxel size. The curves have been multiplied by the relative in vivo MR signal to allow direct comparison. For each value of voxel size the simulation has adjusted TR, TE, flip angle, and bandwidth to maximize image SNR. Image SNR increases with voxel size not only because the voxels are larger but because gradient demands are reduced allowing the simulation to choose different optimized imaging parameters. The simulation suggests that images with SNR's comparable to the "Unit Proton SNR" can be achieved in humans at 1.5 T with $^{23}$Na voxels of 7×7×7 mm and $^{39}$K voxels of 26×26×26 mm.

Another interesting result of the simulation is that given the parameters of Tables 2 and 3 and assuming everything is run at the optimal bandwidth, one can estimate how large the $^{23}$Na and $^{39}$K voxels would need to be to obtain an image SNR equal to the Unit Proton SNR. To make this comparison, the relative MR sensitivities given in Table 1 were taken into account to allow direct comparison to protons and an imaging time of 30 minutes was assumed for $^{23}$Na and $^{39}$K. The results are shown in FIG. 4. For both nuclei, image SNR increases with voxel size not only because the voxels are larger but also because larger voxels decrease gradient demands which can affect bandwidth, TE, TR, and flip angle (all of which are continuously adjusted by the optimization algorithm). From FIG. 4, the simulation predicts that at 1.5 T it should be possible to acquire a $^{23}$Na image with 7×7×7 mm spatial resolution and a $^{39}$K image with 26×26×26 mm resolution in 30 min.

When compared to a reference proton image (Unit Proton SNR), the simulation predicted that $^{23}$Na imaging of the human heart at 1.5 T should in principle be possible with 7×7×7 mm resolution in 30 min (FIG. 4). Experimentally, a similar result (6×6×12 mm resolution in 15 min, FIG. 5). Therefore, despite the fact that the simulation did not take into account important but difficult to quantify differences between proton, sodium, and potassium imaging such as RF coil performance, the simulation provides a useful mathematical framework for evaluating strategies for $^{23}$Na and $^{39}$K imaging.

Potassium Imaging

Unlike $^{23}$Na MRI, $^{39}$K MRI does not appear to be clinically feasible even with the use of optimized imaging parameters. The simulation results suggested that human $^{39}$K imaging at 1.5 T in 30 min would require voxel dimensions of 26×26×26 mm (FIG. 4) which is too large to be clinically useful. In light of the agreement between the simulation and experimental results for sodium imaging, therefore, potassium imaging was not evaluated experimentally. Interestingly, SPECT and PET image resolutions are typically 10–15 mm (detector limit, full width at half maximum). Therefore, the results suggest that if an additional 8-fold increase in SNR were available, $^{39}$K MRI should be possible in 30 min with a spatial resolution similar to PET and SPECT (26×26×26/13×13×13 mm=8-fold). However, other factors such as "invisible" intracellular potassium Fossel, E. T. and Hoefeler, H. Observation of intracellular potassium and sodium in the heart by NMR: a major fraction of potassium is "invisible". *Magn. Reson. Med.* 3:534–540, (1986), Pike, M. M., Frazer, J. C., Dedric, D. F., Ingwall, J. S., Allen, P. D., Springer Jr., C. S. and Smith, T. W. $^{23}$Na and $^{39}$K nuclear magnetic resonance studies of perfused rat hearts. Discrimination of intra- and extracellular ions using a shift reagent. *Biophys. J.* 48:159–173, (1985)) and substantially different design criteria for low frequency RF coils Vlaardingerbroek, M. T. and den Boer, J. A. *Magnetic Resonance Imaging,* Berlin:Springer-Verlag, 1996), The *ARRL Handbook For Radio Amateurs,* Newington, Conn.: American Radio Relay League, 1996.) (the $^{39}$K frequency is 2.98 MHz at 1.5 T) make it difficult to predict the precise amount of additional SNR needed to make $^{39}$K MRI clinically practical.

Choice of Pulse Sequence

The results suggest that high speed GRE pulse sequences employing partial flip angle RF excitation are best suited for $^{23}$Na and $^{39}$K imaging. In addition, 3D rather than 2D imaging appears to have considerable benefits including full volume coverage in the same imaging time, the ability to post-process the data to yield arbitrary slice orientation, and a reduction in TE due to the use of a non-selective square RF pulse. Furthermore, the ability to use a non-selective RF pulse for 3D imaging was helpful in modifying the 1.5 T clinical scanner for $^{23}$Na imaging because it was unnecessary to interface to the Siemens hardware for pulse shaping.

Only rectilinear k-space sampling schemes were studied. Other approaches, such as 3D projection reconstruction (Boada, F. E., Christensen, J. D., Huang-Hellinger, F. R., Reese, T. G. and Thulborn, K. R. Quantitative in vivo tissue sodium concentration maps: the effects of biexponential relaxation. *Magn. Reson. Med.* 32:219–223, (1994), Boada, F. E., Gillen, J. S., Shen, G. X., Chang, S. Y. and Thulborn, K. R. Fast three dimensional sodium imaging. *SMR Proceedings* 2:1195, (1995)) have been used for $^{23}$Na imaging. Projection reconstruction may be particularly useful for quantification of sodium concentrations because of the short TE which can be achieved Boada, F. E., Gillen, J. S., Shen, G. X., Chang, S. Y. and Thulborn, K. R. Fast three dimensional sodium imaging. *SMR Proceedings* 2:1195, (1995)).

Spin echo imaging was not investigated for $^{23}$Na or $^{39}$K for several reasons. First, the use of a surface coil for RF transmission is difficult for spin-echo imaging, due to an inhomogeneous RF field. Second, because the specific absorption rate (SAR) of RF energy increases quadratically with flip angle, the SAR for spin-echo imaging would be roughly 5 times greater than for gradient-echo imaging. Third, $T_2$ relaxation times are so short for $^{23}$Na and $^{39}$K that, at least in theory (see Table 2), the $T_2$* values for these nuclei are nearly the same as $T_2$ for magnetic field inhomogeneities expected on clinical systems. Consequently, signal at a given TE will be nearly the same for spin-echo compared to gradient-echo. Furthermore, since spin echo has a larger TE because of the 180° pulse, the SNR/time will likely be lower.

Optimal Imaging Parameters

An important finding of the present study is that the optimal receiver bandwidth can be directly calculated from $T_2$*. As shown in FIG. 3, for both $^{23}$Na and $^{39}$K the bandwidth at which SNR/time is maximized is limited by the point at which bandwidth per pixel begins to exceed the line width ($1/T_2$*). This implies that an important first step for $^{23}$Na and $^{39}$K imaging is to collect an FID for the particular experimental setup; shim if possible; measure the $T_2$* from the FID decay; and set the imaging bandwidth to $N_{ro}/T_2$*. This finding has two other important implications. First, additional signal may be obtained if shimming of the static field is performed prior to each imaging session. Second, imaging at higher fields (say 4 T rather than 1.5 T) may not increase the acquired $^{23}$Na and $^{39}$K signals as much as might be expected, because in general $T_2$* tends to shorten at higher fields. The shorter $T_2$* may cancel the signal gained by going to the higher field.

Interestingly, it was found experimentally that the $^{23}$Na $T_2$* in humans at 1.5 T was only about 10 msec, whereas a value of 25 msec was expected (Table 2). Unfortunately, attempts to improve $T_2$* by shimming the $^{23}$Na signal were not made because manual shimming was not available on our system. Recalculation of the results of FIG. 3 with $T_2$*=10 msec, however, showed similar results and the optimal SNR/time was still limited by the blurring constraint, Bandwidth>$N_{ro}/T_2$*.

Gradient Performance

The simulation results showed that although demands on gradient hardware for $^{23}$Na and $^{39}$K imaging can be considerable, the SNR penalty for poor gradient hardware is modest. This is largely because SNR/time is maximized for low bandwidths (FIG. 3) resulting in a low amplitude of the readout gradient. In addition, low bandwidth increases TR and yields a lower duty cycle. Nevertheless, good gradient performance is useful in reducing phase and slice encoding times resulting in shorter TEs, which can result in measurable increases in SNR due to the short $T_2$ and $T_2$* of $^{23}$Na and $^{39}$K.

Gradient performance may be more important for $^{39}$K than for $^{23}$Na, largely because of the low gyromagnetic ratio of $^{39}$K (20 times lower than $^1$H, Table 2). In practice, this is not a problem because $^{39}$K voxels must be relatively large, which reduces gradient demands, due to the small MR signal. Nevertheless, it appears that even if additional $^{39}$K signal were available, small voxels for $^{39}$K imaging would be difficult to achieve due to current limitations of the gradient hardware.

RF Considerations

The studies herein used a surface RF coil for transmission and detection. In general, the use of surface coils results in image SNR being a function of distance from the coil, suggesting in the case of cardiac imaging that the posterior wall of the heart will be darker than the anterior. Interestingly, however, at least in theory this appears to be much less of a problem for $^{23}$Na and $^{39}$K imaging than for $^{1}$H. Because of the short $T_1$ of $^{23}$Na and $^{39}$K, the MR signal for these nuclei is relatively independent of flip angle for high speed GRE imaging. For example, for FLASH imaging of $^{23}$Na (FIG. 1b), the signal increases from 35 to 45% of $M_O$ as flip angle decreases from 90 to 40°. Consequently, if RF power is adjusted such that a 90° flip angle is achieved in the anterior myocardium, the signal from the posterior myocardium will be 28% larger (assuming a constant spin density) even if a flip angle of only 40° is realized at the posterior wall (FIG. 1), potentially offsetting the signal loss due to the distance away from the coil.

For human imaging, it is important to ensure that the Food and Drug Administration (FDA) limit for Specific Absorption Rate (SAR) of RF energy is not exceeded (8 Watts/kg for a localized coil). SAR is proportional to the square of RF power ($B_1$) and the square of frequency ($\omega$), $\omega^2 B_1^2$ Perman, W. H., Turski, P. A., Houston, L. W., Glover, G. H. and Hayes, C. E. Methodology of in vivo humans sodium imaging at 1.5 T. *Radiology* 160:811–820, (1986), Vlaardingerbroek, M. T. and den Boer, J. A. *Magnetic Resonance Imaging,* Berlin:Springer-Verlag, 1996). For a constant flip angle and square pulse duration, the required $B_1$ varies inversely with γ, i.e. a $^{23}$Na pulse requires 3.8 times more RF power than a similar $^{1}$H pulse. The increase in RF power, therefore, exactly cancels the decrease in SAR due to the lower $\omega$ of $^{23}$Na as pointed by Perman et al. Methodology of in vivo humans sodium imaging at 1.5 T. *Radiology* 160:811–820, (1986). Consequently, at a given field SAR is independent of nucleus type. Therefore, to examine the SAR for human $^{23}$Na images, the identical imaging pulse sequence was run at the $^{1}$H frequency. The Siemens software reported a localized SAR of 0.75 W/kg for the quadrature head coil. Doubling this value to account for the fact that the coil was not quadrature suggests that the localized SAR for our $^{23}$Na images was about 1.5 W/kg, i.e. well below the FDA limit.

Figure 6:
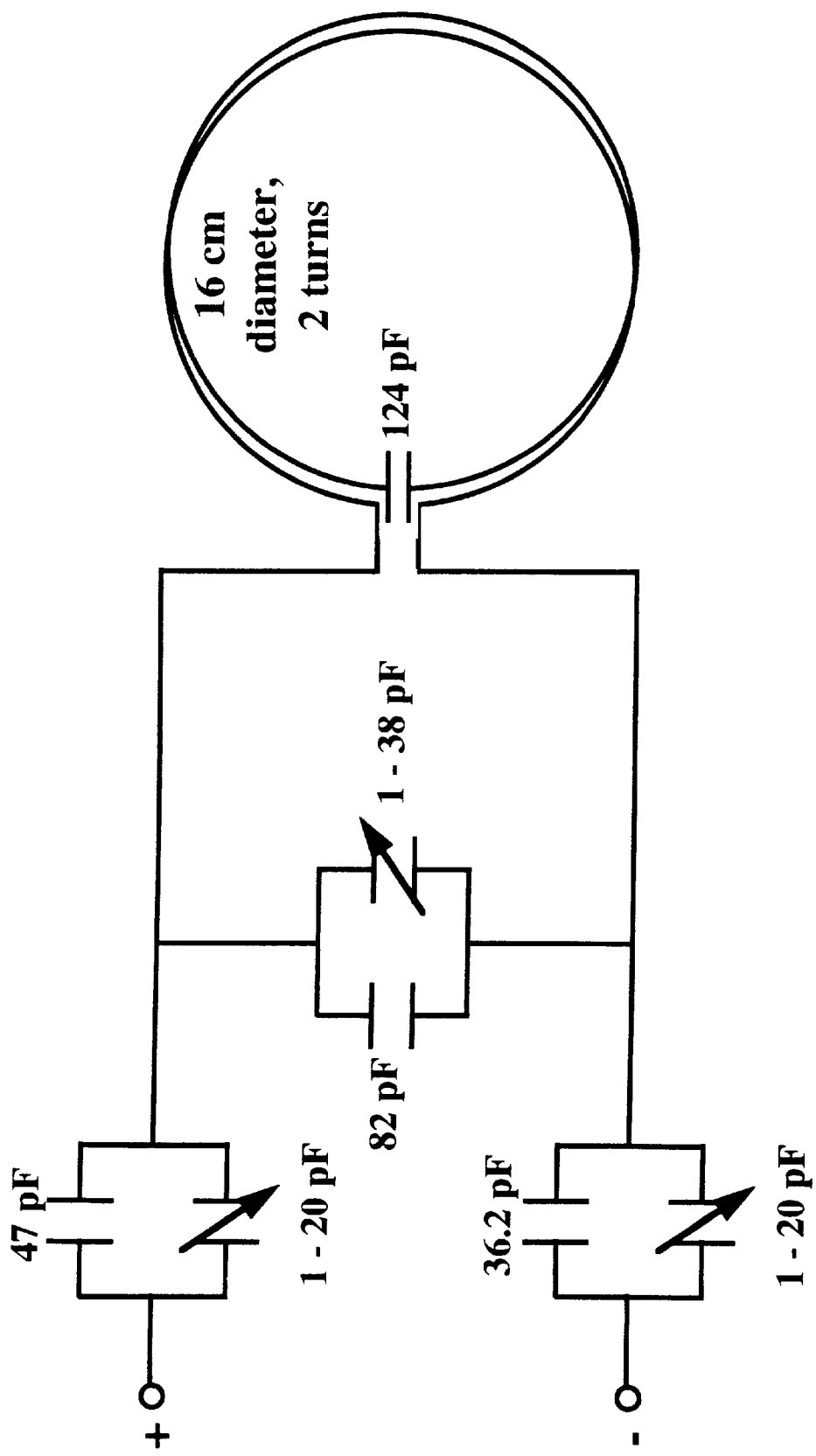
FIG. 6 shows the circuit diagram of RF coil used for $^{23}$Na imaging in humans at 1.5 T.

The RF coil used in the present study FIG. 6 is probably far from optimal. Direct application of surface coil technologies such as the use of distributed capacitance and a quadrature design would likely yield a significant increase in $^{23}$Na and $^{39}$K signal. In addition, due to the low resonant frequencies of these nuclei the use of superconducting RF coils (Black, R. D., Early, T. A., Roemer, P. B., Mueller, O. M., Mogro-Campero, A., Turner, L. G. and Johnson, G. A. A high-temperature superconducting receiver for nuclear magnetic resonance microscopy. *Science* 259:793–795, (1993)) for $^{23}$Na and $^{39}$K imaging may yield a considerable reduction in the noise.

In summary, optimization of imaging parameters dramatically improves $^{23}$Na and $^{39}$K imaging efficiencies and may make human $^{23}$Na imaging of the heart practical in a clinical setting. Because Na$^+$ is directly involved with cellular metabolism, the potential utility of $^{23}$Na imaging for the non-invasive examination of pathophysiologic changes in humans warrants further study.

In addition, the present invention provides a process of identifying regional areas of myocardial damage in vivo. The process includes the step of imaging the heart in vivo using $^{23}$Na or $^{39}$K magnetic resonance imaging wherein regions of relative high image $^{23}$Na intensity and regions of relative low $^{39}$K intensity indicate the damages regions. The damaged regions of the myocardium are non-viable tissue resulting from any pathological condition such as ischemia. $^{23}$Na and $^{39}$K images are obtains using fast gradient echo imaging techniques optimized to maximize signal acquisition by exploiting the short $T_1$ of $^{23}$Na and $^{39}$K thereby reducing imaging times to a few minutes.

Where the heart is imaged using $^{23}$Na imaging, that imaging is accomplished using a) an imaging time of from about 3 minutes to about 20 minutes; b) about 16 phase encodes per cardiac cycle; c) an echo time of from about 2.5 milliseconds to about 6.5 milliseconds; d) a repetition time of from about 8 milliseconds to about 20 milliseconds; e) a signal averaging of from about 200 to about 300; and f) a voxel size of about 1.0–1.5×2.0–3.0×4.0–8.0 millimeters.

Preferably, the imaging time is from about 6 to about 15 minutes, more preferably from about 8 to about 12 minutes and, most preferably about 10 or 11 minutes. The echo time is preferably from about 3.5 milliseconds to about 5.5 milliseconds and, more preferably about 4.5 milliseconds. The repetition time is preferably from about 10 milliseconds to about 15 milliseconds and, more preferably about 13 milliseconds. The signal averaging is preferably from about 225 to about 275 and, more preferably about 256. A preferred voxel size is about 1.25×2.5×6 millimeters.

Using a $^{23}$Na imaging process of the present invention (See the Examples to follow for precise details), eighteen rabbits underwent in situ coronary artery occlusion and reperfusion. To examine $^{23}$Na image intensity in viable and non-viable regions, in situ myocardial infarction and reperfusion was followed by $^{23}$Na imaging of either isolated rabbit hearts (n=6) or in vivo rabbit hearts (n=6). To examine regional sodium content, $^{23}$Na MR spectroscopy was performed on tissue samples from all 6 in vivo rabbit hearts and an additional 6 isolated rabbit hearts subjected to the same infarction/reperfusion protocol. In 4 of the 6 isolated rabbit hearts, $^{23}$Na relaxation times ($T_1$ and $T_2$) were also measured in the tissue samples. To evaluate image quality in both small and large animals, in vivo $^{23}$Na images of normal rabbits (n=6) and dogs (n=4) were acquired. All in vivo $^{23}$Na MRI was performed in closed-chest, cardiac-gated animals.

Image intensity of non-viable myocardium was 42±5% higher than that of viable myocardium in isolated hearts and 95±6% higher in vivo. Spectroscopy results showed that non-viable tissue had on average a 63±8% increase in [Na$^+$] compared to viable tissue in isolated hearts and 142±7% increase in vivo, showing that the differences in image intensity were due to differences in myocardial [Na$^+$]. Similarly, previous studies have also shown increased tissue [Na$^+$] in infarcted, reperfused myocardium by in vitro techniques such as flame emission photometry. The finding that image intensity differences were smaller than postmortem sodium concentrations could be explained by differences in tissue $^{23}$Na relaxation characteristics: both $T_1$ and $T_2$ in non-viable myocardium would have opposite effects on image intensity, with shorter $T_1$ increasing image intensity and shorter $T_2$ (along with $T_2$*) decreasing image intensity. Nevertheless, despite the fact that generated images have some $T_1$, $T^2$, and $T_2$, weighting, the data suggest that regional differences in tissue sodium concentration are so large that tissue [Na*] dominates image intensity. Partial volume effects, in which relatively large imaging voxels contain both non-viable and viable myocardium, is an additional factor which could lead to smaller differences in image intensity compared to differences in image intensity compared to differences in tissue [Na*].

A voxel of normal myocardium would likely have a sodium concentration of 37 mM, assuming 77% of the tissue is water, 75% of the water space is intracellular, $[Na*]_i=15$ mM and $[Na*]_o$ 145 mM. The spectroscopy results for the in vivo experiments reported herein showed virtually the same value (38±1 mM, FIG. 9). In isolated hearts, however, the value was higher (61±2 mM). The elevation in [Na*] in isolated hearts was likely due to edema formation, as suggested by our measurement of tissue water content in isolated hearts of 85±0.3% compared to ca. 77% in vivo. Elevated intracellular [Na*] in the isolated hearts may also have contributed. In non-viable myocardium, [Na*] was 99±4 mM in vivo. These values are close to the value one would estimate assuming all myocytes in the non-viable region failed to maintain a sodium concentration gradient, namely 112 mM (0.77*145=112, assumes 77% of tissue is water, plasma [Na*]=145 mM).

Figure 8:
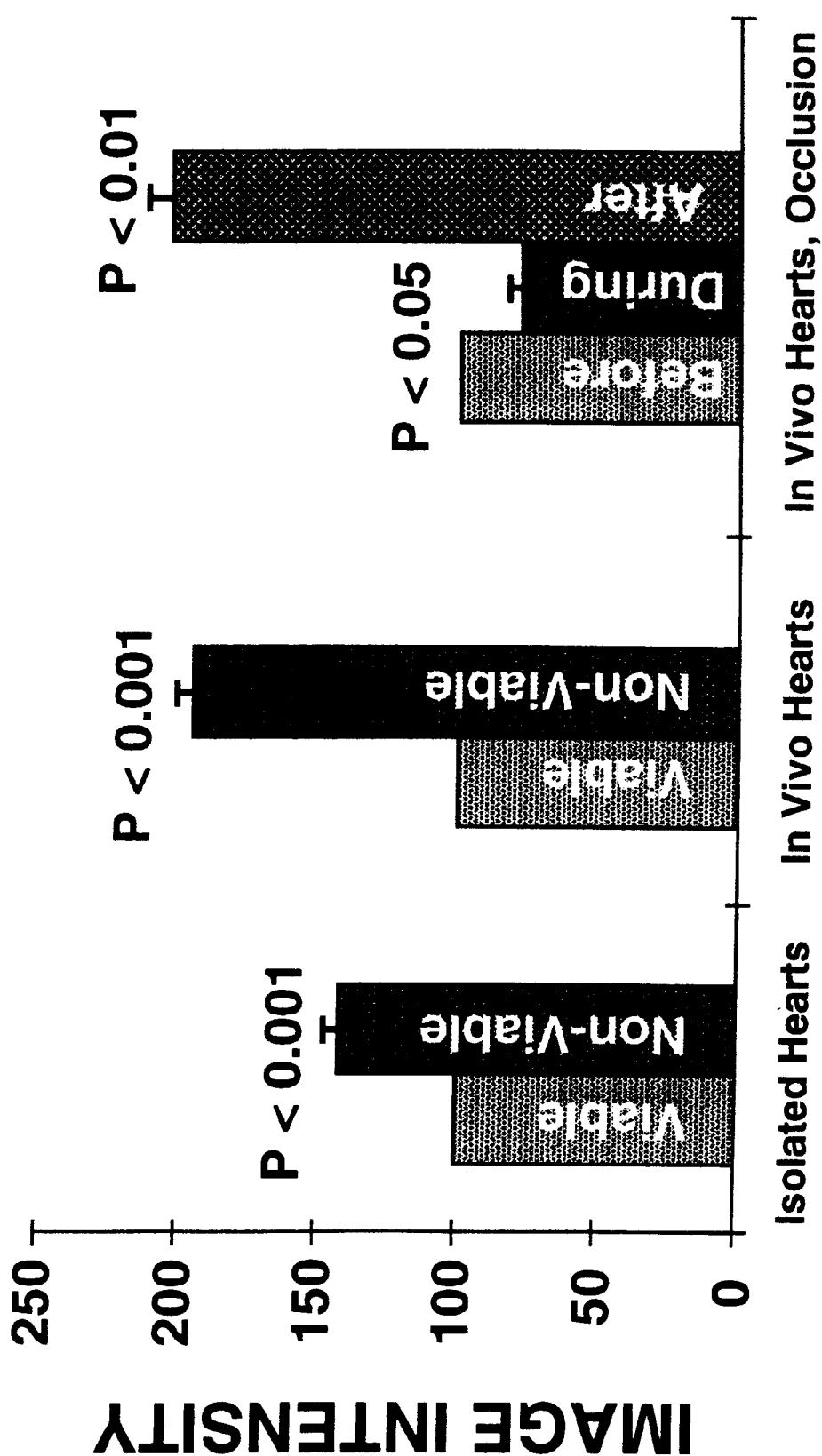
FIG. 8 shows a summary of $^{23}$Na image intensity in viable (TTC positive) and nono-viable (TTC negative) myocardium in all isolated rabbit hears (n=6), all in vivo rabbit hearts with images acquired at the same location before, during, and after closed-chest coronary artery occlusion (n=3). Intensity was normalized to either remote (viable) regions or pre-occlusion intensity.

Increases in tissue Na* in non-viable regions, however, require sodium delivery via microvascular perfusion. Jennings et al. have clearly shown that infarcted tissue without reperfusion may take several hours for total tissue sodium to rise since electrolyte delivery would depend on slow ion diffusion. FIG. 8 shows that $^{23}$Na image intensity decreases (22±4%, p<0.05) during complete ischemia, perhaps secondary to decreases in vascular and/or interstitial volumes (which contain high [Na*]) caused by reduced perfusion. Although "no-reflow" zones in the core of the infarct could also limit electrolyte delivery to infarcted myocardium, recent studies suggest that regional no reflow due to microvascular damage or stasis from intravascular neutrophil accumulation is a progressive phenomenon that develops during the perfusion period in areas that initially received adequate reperfusion.

In the present study, the composite sodium signal was obtained without differentiation between intracellular and extracellular signals. In general, relating $^{23}$Na image intensity to myocardial viability is considerably complicated by the contribution of extracellular Na* to image intensity. For example, because extracellular [Na*] is normally much greater than intracellular [Na*], even a small increase in extracellular volume due to edema may significantly elevate $^{23}$Na image intensity while intracellular [Na*] remains near normal levels. However, in vivo elevations in myocardial image intensity of nearly 100% and postmortem [Na*] of nearly 150%, as found in the present study, would be difficult to explain without postulating substantial intracellular accumulation of Na*.

The present studies are the first to employ recently-developed fast imaging techniques, originally developed for proton imaging, to the sodium nucleus. Using this approach, $^{23}$Na imaging times were reduces to a few minutes with sufficient SNR to examine regional differences in mycardial sodium content. The main features which allowed a reduction in imaging time are: 1) gradient echoes; 2) fractional echoes; 3) extremely short TR; and 4) imaging at the Ernst angle. Although it has been recognized that the $T_1$ of sodium can allow a short TR for signal averaging, previous studies have not attempted partial flip angle, gradient-echo imaging with extremely short TR. We hypothesized that signal could be gained by fast gradient-echo imaging since the short $T_1$ of sodium would allow large tip angle excitations even for fast pulse repetition times. For example, consider a spoiled-GRASS (SP-GR) sequence whose theoretical signal intensity is given by $$M^\circ M_0 \frac{\sin a(1 - e^{-TR/1})}{(1 - \cos a\, e^{-TR/t1})}$$

where a is the flip angle.

Figure 10:
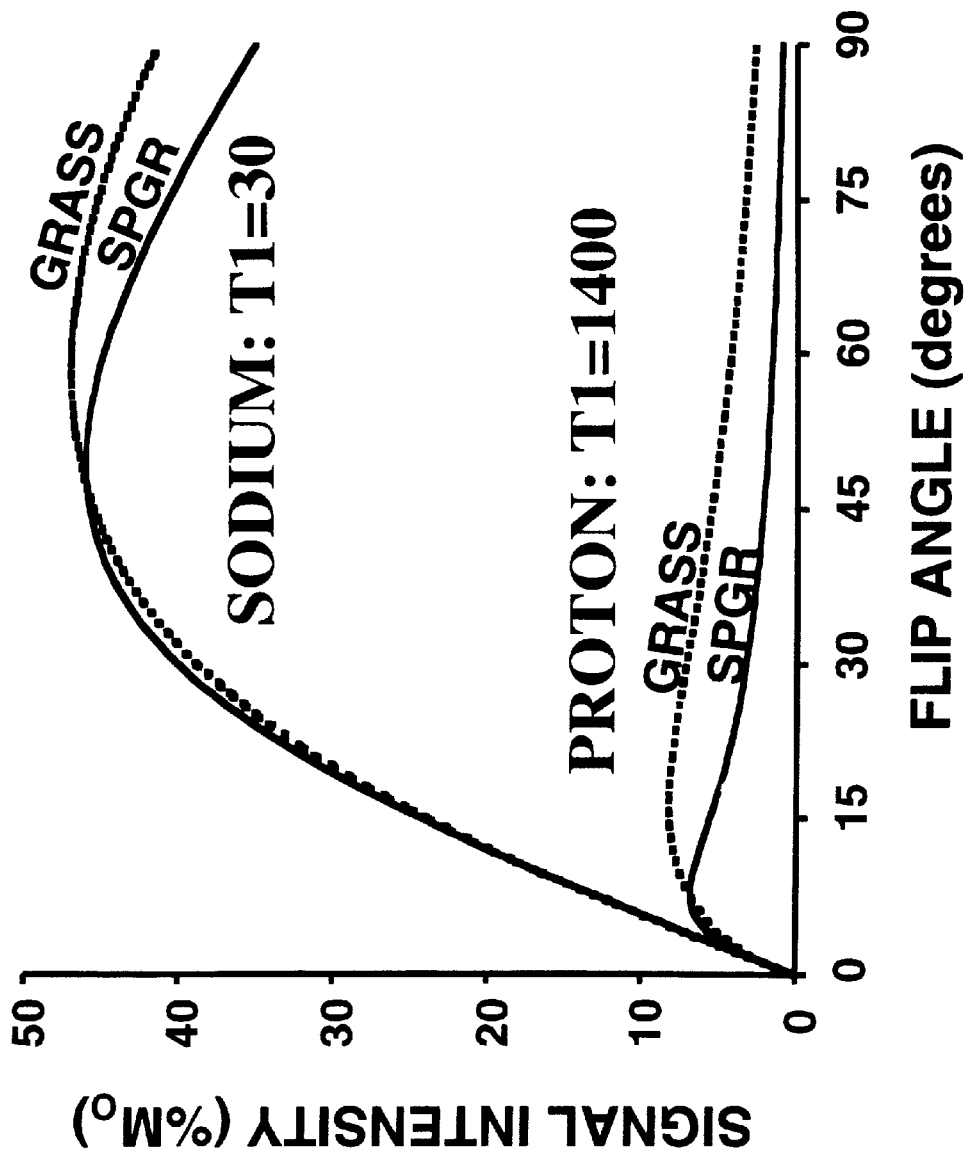
FIG. 10 shows a plot of steady-state signal (% of maximum, M$_o$) for spoiled-GRASS (solid lines) and GRASS (dashed lines) as a function of flip angle for T$_1$'s characteristic of protons and sodium at 4.7 T (1400 and 30 ms, respectivly). The curves assume TE=0 and TR=13 ms. The GRASS curves also assume a uniform phase dispersion of isochromats, and T$_2$ values of 60 and 20 ms for protons and sodium, respectively. Note that the angle at which signal is maimized (Ernst angle) is much larger for sodium (50° vs. 8° for spoiled-GRASS; 59° vs. 16° for GRASS). The observation that peak signal is approximately 6-fold higher for sodium compared to protons suggests that fast gradient-echo techniques are much more efficient for sodium than for proton imaging.

FIG. 10 (solid lines) shows the solution to this equation for a TR of 13 ms and $T_1$ values similar to those of protons and sodium at 4.7 T (1400 and 30 ms, respectively). Note that at the peak of the sodium curve the gradient-echo sequence collects 48% of the total theoretical $^{23}$Na signal every 13 ms, compared to only 8% for $^1$H, a 6-fold increase. Computer stimulation of the phenomenological Bloch equation for steady-state coherent sequences such as GRASS showed a similar increase in signal (FIG. 10, dashed lines). Furthermore, compared to classic spin-echo $^{23}$Na imaging with one phase encode per cardiac cycle, gradient-echo techniques allow acquisition of multiple phase encodes per cardiac cycle (16 for in vivo rabbits) and therefore significantly improve the time efficiency of date collection.

To be clinically useful, it is necessary to acquire sodium images of the heart with voxel dimensions a few millimeters on each side and imaging times of a few minutes. Superficially, these requirements would appear very difficult to meet in light of the fact that the sodium MR signals is approximately 10,000 times smaller than that of protons. The result of the studies disclosed herein show that the combination of approaches disclosed herein results in an increase in signal sufficient to achieve the requirements for clinical sodium imaging.

The image signal was increased by working at higher field strength (4.7 T) than conventional scanners (1.5 T). If it is assumed that noise is dominated by losses in the RF receiver coil, then SNR increases with frequency to the 7/4 power. If noise is dominated by sample losses then SNR increases only linearly. Assuming an intermediate frequency dependence of 3/2 power, SNR is 5-fold higher at 4.7 T than at 1.5 T. Second, voxel volume was at least 15-fold higher than is routinely used with proton imaging, corresponding to a 15-fold increase in signal. Third, the signal averaged 256 echoes. Since SNR varies with the square root of the number of averages, this resulted in an additional 16-fold increase in signal. Finally, the addition of a 6-fold increase in signal due to the use of fast imaging techniques applied to the sodium nucleus (FIG. 10), resulted in an improved SNR nearly 4 orders of magnitude (5×15×16×6=7200).

As described in detail hereinafter in the Examples, excellent results were obtained in in vivo dog $^{23}$Na imaging experiments using a surface coil which was too large for the dog but reasonable for humans (15 cm), voxel sizes similar to those which might be useful clinically (3×6×25 mm), and acquired $^{23}$Na images in 4 minutes. Image SNR was similar to routine clinical proton images (20±3 in anterior myocardium), strongly suggesting that existing high field ($\geq$4 T), whole-body magnets could be used to produce $^{23}$Na MR images of the human heart with modest trade-offs in imaging time (minutes) and spatial resolution (voxel dimensions $^3$O15=2.5times larger than protons).

The Examples to follow illustrate preferred embodiments of the present invention and are not limiting of the specification or claims in any way.

EXAMPLE 1

Human Imaging

To allow transmission and reception of RF energy at the $^{23}$Na frequency (16.8 Mhz), a second RF transmit/receive subsystem was constructed and interfaced to a 1.5 T Siemens Vision. The second RF channel consisted of a frequency synthesizer, broadband RF transmitter/receiver, transmit/receive switch, and broadband pre-amp (TecMag, Houston, Tex.), as well as home-built electronics used to interface the Siemens timing signals and RF phase modulation to the transmitter/receiver, and a 1.2 kW broadband RF amplifier (Henry Radio, Palo Alto, Calif.).

A home-built 16 cm diameter $^{23}$Na surface coil was used for imaging. The circuit diagram for the $^{23}$Na coil is shown in FIG. x. The $^{23}$Na coil electronics were contained within a specially-designed Plexiglas housing to protect the volunteer. To allow examination of the location of the $^{23}$Na RF coil with respect to the heart in $^{1}$H scout images, a small chamber was machined into the center of the Plexiglas housing and filled with a solution of saline and 10 mM Gd-DTPA. The Plexiglas housing also contained three 28" long plastic rods to allow adjustment of the tune, match, and balance capacitors of the coil in the magnet without moving the volunteer. Tuning and matching of the coil was verified prior to $^{23}$Na data acquisition using a portable RF sweeper (Model 405NV, Morris Instruments, Gloucester, Ontario, Canada).

Four volunteers were studied. The $^{23}$Na RF coil was first centered on the scan table. Each volunteer was then placed prone over the coil and the volunteer was moved into the magnet. To locate the heart exactly over the center of the $^{23}$Na coil, $^{1}$H scout images were acquired using the body RF coil. The location of the Plexiglas chamber containing the saline/Gd-DTPA solution was examined, and the volunteer was asked to move. The double-oblique plane corresponding to the short-axis of the heart was then established, and a final series of cardiac gated, high-resolution short-axis $^{1}$H images were acquired at six base-apex slice locations encompassing the heart for later comparison to the $^{23}$Na images.

The Siemens $^{1}$H RF channel was then disabled and the second channel RF electronics were used to acquire $^{23}$Na images. An FID was acquired to verify that the system was on resonance and used to determine the global $T_2^*$ of the sodium signal for use in selecting the receiver bandwidth. Next, the RF power level was examined by acquiring a projection image of sodium with the readout direction perpendicular to the plane of the coil. The pulse width was varied until the signal from the heart was maximized. Then, a 3D GRE pulse sequence, identical to that used in the numerical simulations, was used to acquire the $^{23}$Na images with the RF power set to the optimal value determined from the projection images. The $^{23}$Na image planes were prescribed such that the slices of the 3D acquisition corresponded to the short-axis locations of the $^{1}$H scout images. By encoding the 3D $^{23}$Na images in the short-axis orientation, in-plane resolution could be improved at the expense of slice thickness. Imaging parameters used for human $^{23}$Na imaging at 1.5 T were: imaging time 15 minutes; no gating was used; TR 20 ms; TE 3.6 ms; typical RF pulse width 1500 µs; receiver bandwidth 6,250 (±3,125) Hz; $N_{AVG}$=50; matrix size=64×64×14; voxel size=6×6×12 mm.

Figure 5:
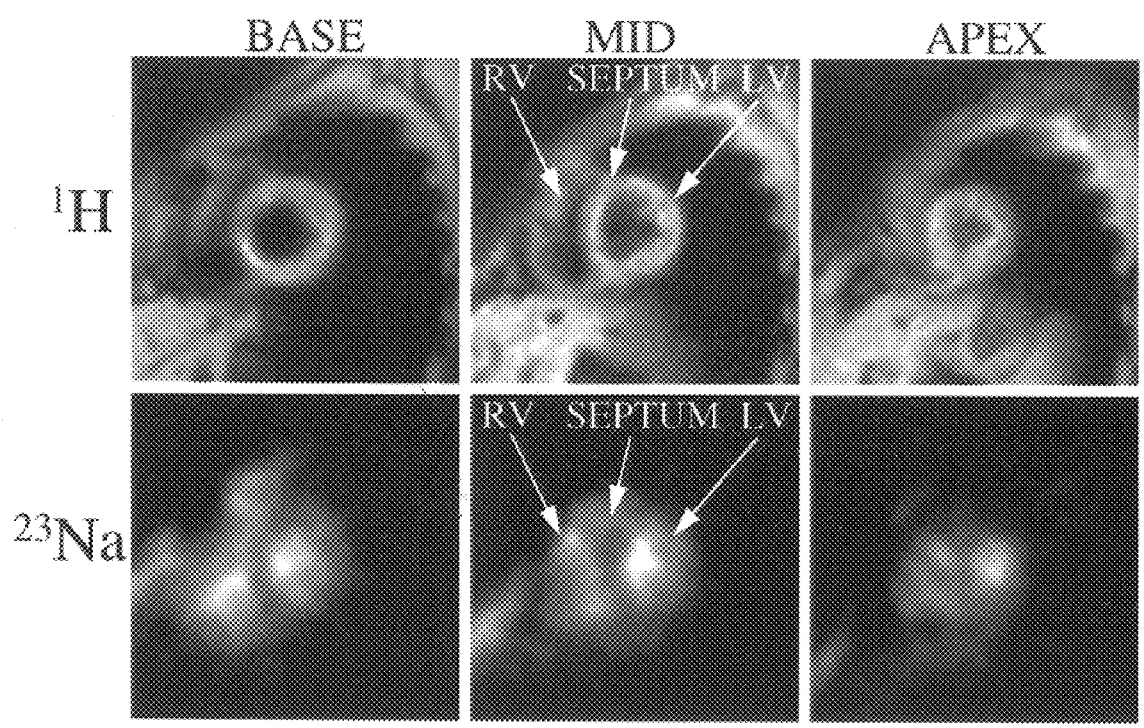
FIG. 5 shows three short axis $^{23}$Na images of an in vivo human heart extracted from a 3D dataset acquired at 1.5 T in 15 min with 6×6×12 mm voxels. The $^1$H images at the same locations are shown for comparison. The myocardium and ventricular cavities were clearly visible in the $^{23}$Na images.

FIG. 5 shows three short axis $^{23}$Na images of a human heart acquired at 1.5 T. The 3D dataset from which these images were extracted was acquired in 15 min. The $^{1}$H images at the same location are shown for comparison. The $^{23}$Na image intensity is elevated in the cavities (blood pool) and the myocardium is clearly visible. The $^{23}$Na SNR's for the images shown in FIG. 5 were 11 in the left ventricular cavity and 7 in the myocardium (septum). Similar results were obtained in each of the three other volunteers.

EXAMPLE 2

General Methods for Viability Studies

MR Imaging and Experimental Protocol

All images were acquired on a GE/Bruker 4.7 Tesla Omega system using a gradient-echo pulse sequence utilizing basic features of gradient-recalled acquisition in the steady state (GRASS). For isolated hearts, the sequence was then continuously. For in vivo imaging, cardiac-gated, segmented k-space data acquisition was used. To decrease $^{23}$Na imaging times, half period sinusoid gradients were used for many of the gradient wave forms including the slice select gradient. In addition, the slice refocus, phase encode, and readout prephaser gradient lobes were chosen to overlap completely, and had a minimum duration determined by the maximum gradient strength and the lobe that required the greatest area. Partial-echo acquisition was employed to further reduce TR and TE. Different gradient sets were use for rabbit imaging. For rabbits, the maximum gradient slew rates and amplitudes were 19.5 Gauss/cm/msec and 3.9 Gauss/cm, respectively. For dogs, the corresponding values were Gauss/cm/msec and 1.2 Gauss/cm.

Image Analysis

Isolated Hearts

Since the epicardial marker had guided selection of both the TTC and MR slice, spatial correlation of the tow images was undertaken. For each heart, the left ventricle (LV) on the digitized TTC stained image was traced by two independent observers using the software package NIH Image on a Macintosh Quadra. The non-viable TTC negative region was also traced. These outlines were superimposed over the MR image which was scaled and rotated appropriately to match the LV borders. The TTC negative outline was the used to draw a comparable re-lon on the MR image. In all cases the reason of altered signal intensity on the MR image was similar in size and location to the region of abnormal TTC staining (see FIG. 7). However, since the LV borders on the MR image were not identical to the TTC image and did not perfectly overlay, observers were instructed to include myocardial regions with obviously altered signal intensities. Regions-of-interest (ROIs) were also selected from remote, viable regions of myocardium. Signal intensities were normalized to the saline standard and averaged for the two observers.

In-Vivo Hearts

For in vivo hearts subject to infraction, ROIs were placed over the infarcted territory (identified by the external marker and postmortem TTC staining) and an adjacent, viable region. In normal animals, ROIs were placed in the anterior myocardium, left ventricular cavity, and posterior myocardium to calculate signal-to-noise ratios (SNR) at these locations.

All Hearts

SNRs were determined using Henkelman's method for magnitude images.

MR Spectroscopy

Tissue samples (350 to 750 mg) were taken from non-viable and viable regions. The non-viable region, distal to the coronary occlusion site, was easily identified by discoloration and the presence of intramyocardial hemorrhage. The tissue samples were blotted dry to remove surface contamination. The circumferential margins of the samples were trimmed 2 mm in case capillary action may have removed tissue water. Samples were weighed and placed in sealed glass tubes. Na$^+$ concentrations of the tissue samples were determined spectroscopically by comparison to the Na$^+$ signal of a reference standard. The standard consisted of a sealed glass tube filled with 1 nil of a solution containing 109 mM Na$^+$ and 43.5 mM dysprosium triethylenetetraminehexaacetic acid 14 (Dy-TTHA). The Dy-TTHA was used to shift the $^{23}$Na peak of the standard such that two $^{23}$Na peaks would appear in the spectrum: one peak from the glass tube containing the tissue and one pak from the Class tube containing the Dy-standard. Care was taken to place the tissue sample and the adjacent Dy-standard entirely within the RF $^{23}$Na spectra were acquired using a 90$^+$ pulse (45 $\mu$Ls), a pre-acquisition delay of 58 $\mu$s, a data six of 1 K, an aquision of time of 100 ms, 512 averages, and a repetition rate of 250 ms to allow complete relaxation between pulses. Tissue [Na$^+$] was calculated as: (area under tissue peak/area under standard peak)*109 mm*(1 g/tissue sample weight). The results were express as mM Na$^+$ and assume 100% visibility for all sodium signals. The spectroscopic method above $^{23}$Na was validated by measuring sodium concentration in five test tubes containing known concentrations of sodium. The r value relating known to measured [Na$^+$] was 0.99.

T1 and T2 Determination

Relaxation times were measured for total (intracellular plus extracellular) myocardial sodium. $T_1$ values were obtained using standard inversion recover, with inversion time ranging from 1 to 250 ms (9 data points). A Hahn spin-echo pulse sequence with echo times ranging from 0.5 to 40 ms used to measure $T_2$ (11 data points). For both experiments there were 64 averages with a pre-delay of 250 ms. All signals were analyzed as the area under the peak in the frequency domain. The $T_1$ data were fit to a single exponential. The $T_2$ data were fit to a double exponential using the equation.

$$M = M_{fast} \exp(-TE/T2fast) + M_{slow} \exp(-TE/T2slow)$$

where $M_{fast}$ ($M_{slow}$) represents the magnitude of the signal with time constant $T2_{1fast}$ ($T_{slow}$) and where TE is the echo time. The sum of the coefficients $M_{fast}$ and where TE is the echo time. The sum of the coefficients $M_{fast}$ and $M_{slow}$ was constrained to equal 1.0.

Tissue Water Content

In the isolated hears, we/dry weights of viable and non-viable myocardium were measured by desiccation in a heating oven at 50° C. for at least 36 hours to determine if differences in tissue sodium content could be explained by edemana Statistical Analysis All results were expressed as mean±SEM. Differences between viable and non-viable myocardium in image intensity, sodium content, tissue water content, and relaxation characteristics were assessed using t test. The hypothesis that image intensities in the same region of the same heart varied before, during, and after coronary artery occlusion was assessed using repeated-measures ANOVA. Comparison between MRI and MRS results was accomplished using an unpaired t test for isolated hears and a paired t test for in vivo hearts. Values of $p<0.05$ were considered significant.

EXAMPLE 3

In situ and in vivo $^{23}$Na Imaging

In situ procedures—New Zealand White rabbits (3.5–4.0 kg) were anesthetized with intravenous sodium pentobarbital (ca. 27 mg/kg), intubated, and mechanically ventilated. A median sternotomy was performed, and a reversible snare ligature was placed around an anterior branch of he left coronary artery. After 40 minutes of in situ occlusion followed by 60 minutes of reperfusion, the hearts were rapidly excised and retrogradely perfused with cardioplegic solution at room temperature. An epicardial marker (2-mm. Diameter polyethylene tube filled with saline) was attached to the right ventricle (RV) at the same base-to-apex level as the infarct territory. Pressure was adjusted at the beginning of the experiment of obtain a flow of 10 ml/min (1.0–1.5 ml/min/g, measured with an in-line electromagnetic flowmeter, model 1401, Skalar Medical) and then held constant. Typical perfusion pressures were 35–45 mmHg. The perfusate was not recirculated. Perfusate composition was (in mM): Na$^+$ 120, K$^+$ 16, Mg$^{2+}$ 16, Cl 160, HCO$_3$. The perfusate was equilibrated with 95% O$_2$, 5% CO$_2$, to maintain pH 7.4–7.53. Previous studies show that hearts isolated in this manner remain viable. The hearts were hung vertically in a 30-mm diameter radio frequency (RF) volume coil and placed in the magnet.

A test tube filled with normal saline ([Na$^+$]=154 mM) was placed adjacent to the heart for signal calibration. Left ventricular (LV) short axis $^{23}$Na images were acquired using the epicardial marker to locate the appropriate slice. Imaging parameters were: imaging time 7.1 minutes; TE 4.6 ms; TR 13 ms; $N_{AVG}$=256; matrix size=256×128; voxel size=0.6× 1.2×4.5 nun. Imaging was performed at the Ernst angle which was determined empirically.

Following MR imaging, the short axis slice identified by the epicardial marker (ca. 4 mm thick) was incubated in a 1% TTC (triphenyltetrazolium chloride) solution at 37° C.–40° C. for 15 minutes. Since TTC forms a red precipitate in the presence of intact dehydrogenase enzyme systems and reducing coenzymes, viable myocardium stains brick red whereas necrotic areas fail to stain. The TTC stained myocardial slice was photographed, and the resultant 35 mm slides were digitally scanned for subsequent analysis.

In- Vivo Procedures—New Zeland White Rabbit were anesthetized with intramuscular ketamine/xylazine (50 mg/kg and 2.5 mg/kg respectively), intubated, and mechanically ventilated. A catheter was placed in the femoral artery to monitor systemic pressure. A left thoracotomy was performed at the fifth intercostal space. A deflated 2-mm angioplasty balloon catheter was loosely asutured around an anterior branch of the left coronary artery. An epicardial marker filed with saline was placed over the territory perfused by the artery, and a catheter was placed in the left atrium for injection of fluorescent microspheres (15 $\mu$m, Molecular Probes). The chest was then closed in two layers, the rabbits were placed prone on a 5-cm diameter gouble-resonant $^{23}$Na-$^1$H surface RF coil, and placed in the magnet. Using this approach, coronary artery occlusion and reperfusion could be performed closed-chest in the magnet by inflation ad deflation of the ballon.

Femoral artery pressure was used for cardiac gating. Double-oblique, short or long-axis $^1$H images were first acquired using the epicardial marker to identify the to-be-infracted territory. The RF coil was then tuned to the $^{23}$Na frequency and a control $^{23}$Na frequency and a control $^{23}$Na image was acquired at the same location. $^{23}$Na imaging parameters were: imaging time 11 minutes; 16 phase encodes/cardiac cycle (gated to end-diastole); TE 4.6 ms; TR 13 ms; NAIG+256: matrix size+256×128 voxel size 1.25×2.5×6 mm.-Heart rate in these anesthetized rabbits was approximately 180 BPM. A control set of microspheres was injected into the left atrium. The balloon catheter was then inflated to produce coronary artery occlusion for 40 minutes, a second set of microspheres injected, and another $^{23}$Na image was acquired. The balloon was then deflated to allow reperfusion, a third set of microspheres injected, and another $^{23}$Na image was acquired. After approximately 60 minutes of reperfusion, a final set of microspheres was injected and a final $^{23}$Na image acquired. The hears were then removed and sectioned at the level of the epicardial marker. One side of the heart was stained with TTC to verify the location and extent of infarction. The other side of the heart was used to obtain tissue samples from infarcted and normal regions for spectroscopic analysis of sodium content (see MR Spectroscopy) and for Microsphere flow determination.

Normal Animals—To explore the clinical potential of sodium imaging, we acquired in $^{23}$Na images in normal rabbits (n=6) and dogs (n=4). Normal rabbits were imaged using the same methodology used for animals subject to infaction. Normal mongrel dogs (20–25 kg) were anesthetized with sodium pentobarbital and intubated. After a femoral catheter was inserted for cardiac gating, the animals were placed in the left anticubital position on a 15-cm diameter double resonant $^{23}$Na-$^{+}$H surface coil and placed in the magnet. The same pulse sequence was used for dogs.

Double-oblique short axis $^1$H images were first acquired and then followed by $^{23}$Na images at the same location. Dog imaging parameters were: imaging time 4 minutes; 32 phase encodes/cardiac cycle (gated to end-diastole); TE 3.9 ms; TR 8.1 ms; $N_{AVG}$=128; matrix=256×128; voxel size=3×6× 25 mm. Heart rate in these anesthetized dogs was approximately 120 BPM.

Figure 7:
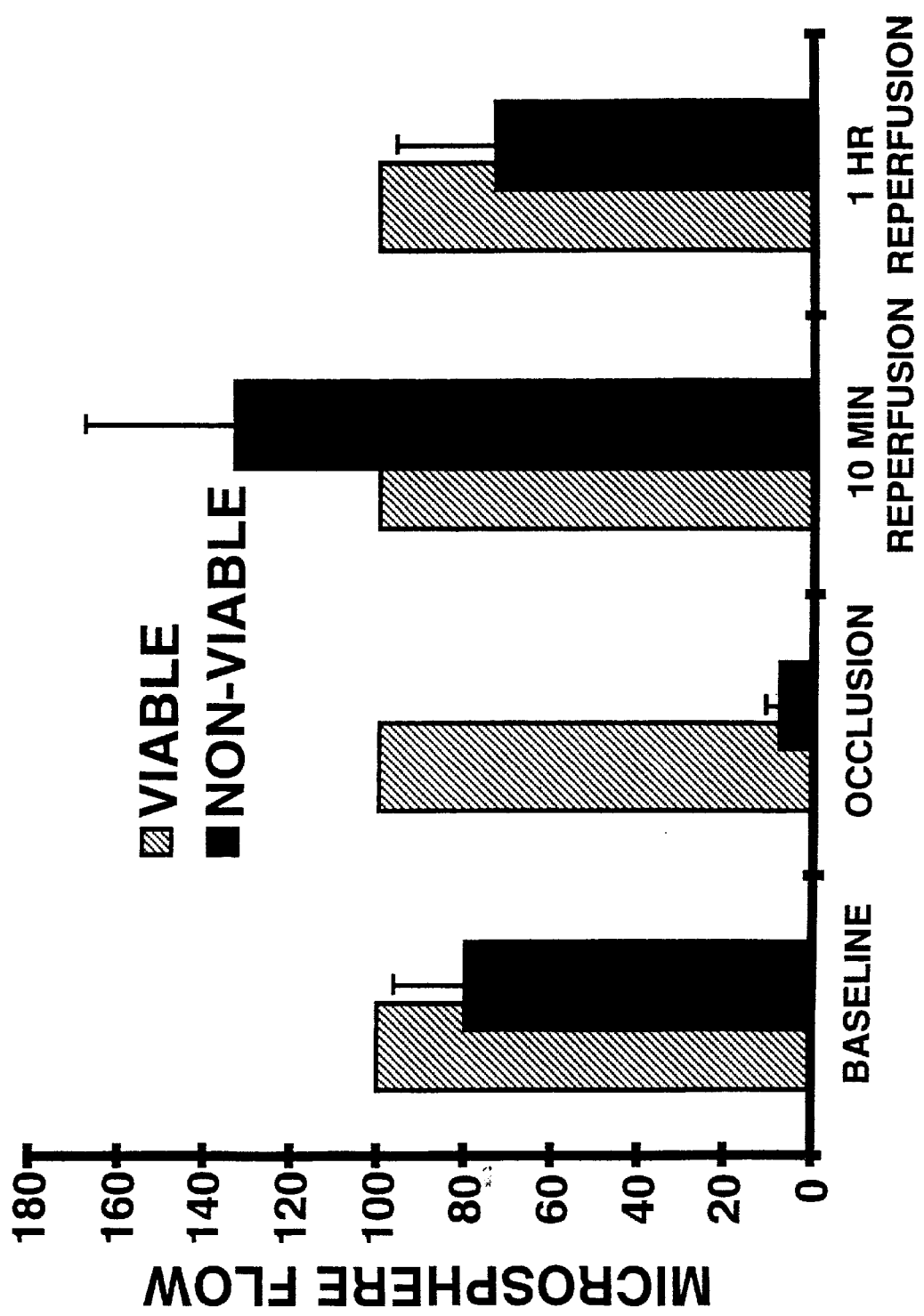
FIG. 7 shows microsphere blood flow in th in vivo rabbits demonstrating succesful closed-chest occlusion and reperfusion performed in the magnet without moving the animals. Data are expressed as percent of blood flow in remote (viable) regions.

The results of these studies are summarized in FIGS. 7–10. FIG. 7 shows microsphere flow for the in vivo animals, demonstrating successful coronary artery occlusion and reperfusion closed chest in the magnet. In all cases, the $^{23}$Na signal was sufficient to generate clear images of both left and right ventricular walls. As expected, the structures with the highest sodium concentration (i.e. the ventricular cavity filled with saline perfusate or blood) had the highest image intensity. Viable myocardium had less signal in comparison, being 48±5% of saline (isolated hearts) and 50±3% of blood (in vivo), consistent with active transport of Na$^+$ out of the myocyte. In non-viable regions, identified by the lack of TTC staining, Na$^+$ image intensity was greater than in viable regions both in isolated hearts and in vivo, consistent with intracellular accumulation of Na$^+$.

In three of the six in vivo animals, Na$^+$ images of the to-be-infarcted territory were acquired before, during, and after coronary artery occlusion. In the remaining three animals, only post-reperfusion Na$^+$ image data were acquired. Before occlusion, image intensity in the to-be-infarcted territory was similar to adjacent, viable regions. During occlusion, Na$^+$ image intensity within the territory decreased by 24% in this animal. Following 1 hour of reperfusion, image intensity within the territory increased by 96%.

FIG. 8 summarizes the image intensity results. In isolated hearts, image intensity was 42±5% greater in non-viable vs. Viable myocardium (p<0.02). For in the in vivo hearts, the elevation was 95±6% (p<0.001). For the three hearts in which Na$^+$ images were acquired before, during, and after coronary artery occlusion, Na$^+$ image intensity fell by 22±4% (p<0.05) during occlusion and rose by 104±8% (p<0.001) following one hour of reperfusion.

Figure 9:
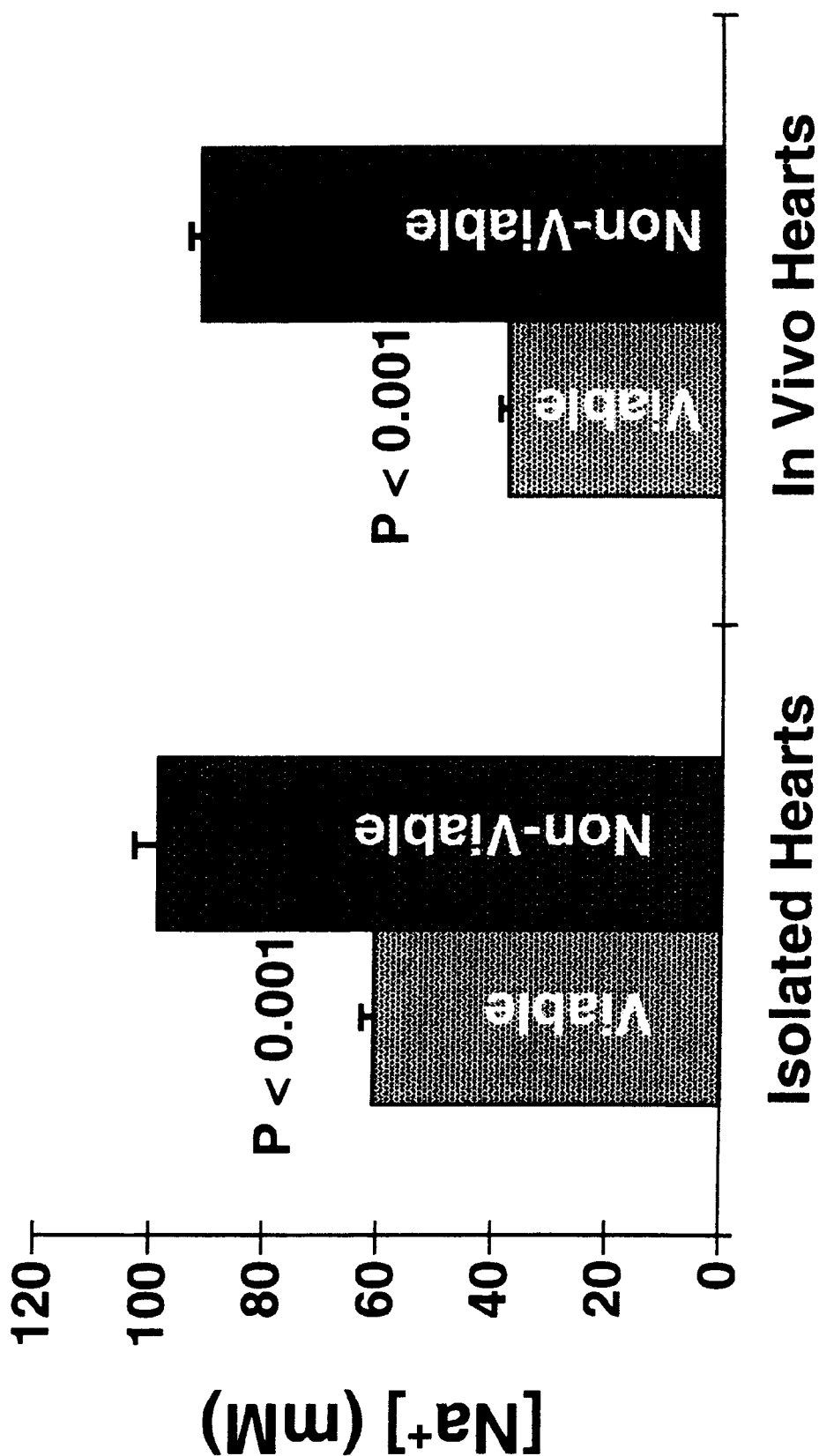
FIG. 9 shows a summary of sodium content measured by spectroscopy in isolated hearts and in postmortem tissue samples from the in vivo hearts. [Na$^+$] was higher than viable tissue [Na$^+$].

FIG. 9 shows the composite sodium concentration (intracellular plus extracellular) of non-viable myocardium compared with viable myocardium for the isolated and in vivo hearts. Sodium content was significant higher in non-viable tissue (isolated: 99±4 mM, in vivo: 91±2 mM) compared to viable tissue (isolated; 61±2 mM, in vivo: 38±1 mM, p<0.001 for both). The elevation in sodium concentration between non-viable and viable myocardium measured by spectroscopy (isolated: 63±8%, in vivo: 142±7%) was larger than the elevation in image intensity measured by MRI (isolated: 42±5%, in vivo 95±6%, p<0.05 for both).

All $T^1$ relaxation data were well characterized by a single exceptional decay. The measurement $T^1$ and $T^2$ values of the Dy-standard were nearly the same with each experiment demonstrating the reproducibility of the measurements. The mean $T^2$ of the Dy-standard was near the means T, value although it was slightly decreased (28.2±0.3 ms vs. 29.2±0.3 ms; p<0.001). Likewise, the slow component of $T_2$ for both non-viable (21.9±1.2 ms) and viable (31.5±0.8 ms) tissue approached the $T_1$ values (26.2±1.5 ms and 34.2±0.9 ms, respectively) although they were consistently less (p<0.01 for both). The $T_1$ of viable tissue (34.2±0.9 ms); p<0.005. Similarly, both the fast and slow component of non-viable tissue $T_2$ were found to be shorter than viable tissue $T_2$, although only difference in $T_{2slow}$ reached statistical significance ($T_{2fast}$: 2.2±0.2 ms vs. 3.6±0.6 ms, p=NS; $T_{2slow}$: 21.9±1.2 ms vs, 31.5±0.8 ms; p<0.001). The magnitude of the fast component as a percentage of the total signal was not significantly different between non-viable and viable tissue (26±5% vs. CD 22±1%).

In the isolated hearts, there were not significant differences in tissue water content between non-viable and viable myocardium (84±0.3 vs. 85±0.3 percent water by weight respectively, p=NS).

In-vivo sodium images of normal rabbits were similar to those in animals subject to infarction. Since a surface coil was used for in vivo imaging, the anterior LV myocardium had higher SNR than the posterior myocardium (rabbits: anterior 12±1, posterior 8±1; dogs: anterior 20±3, posterior 11±2). Compared to rabbits, we obtained in vivo sodium images in dog's with a shorter imaging time (4 minutes vs 11 minutes) and almost twice the SNR, most likely because larger animals allow the use of larger voxels. The imaging parameters in dogs were chosen to allow estimations of voxel sizes, imaging times, and image quality in humans.

EXAMPLE 4

$^{23}$Na and $^{39}$K Imaging Studies

To evaluate in vivo $^{23}$Na and $^{39}$K imaging, three surface RF coils were constructed: a 5 cm diameter $^{23}$Na-$^1$H coil for rabbit imaging at 4.7 T; a 4 cm diameter $^{39}$K-$^1$H coil imaging at 4.7 T, and a 15 cm diameter $^{23}$Na coil for human imaging at 1.5 T. To evaluate the performance of each coil, the unloaded and A loaded "Q" values were evaluated at $^{23}$Na or $^{39}$K frequency on a Hewlett-Packard Spectrum Analyzer.

New Zealand White rabbits were anesthetized with intramuscular ketamin/xylazine (50 mg/kg and 2.5 mg/kg respectively), intubated, and mechanically ventilated. Anesthesia was maintained by isoflurane using a pediatric anesthesia machine. A catheter was placed in the femoral artery for cardiac gating and to monitor systemic pressure. All images were acquired on a GE/Bruker 4.7 Tesla Omega system using a 3D gradient-echo pulse sequence. For $^{23}$Na imaging, the rabbits were placed prone on a 5-cm diameter dual-tuned $^{23}$Na $^1$H surface RF coil (one peak at 52.9 Mhz and one at 200), and placed in the magnet. For $^{39}$K Imaging, a 4-cm diameter dual-tuned $^{39}$K-$^1$H surface RF coil was used (one peat at 9.34 Mhz and one at 200). Cardiac-gating was used in all cases, and approximately 50% of the R—R interval was used to acquire the MR data, gated to end-diastole.

3D $^1$H scout images were first acquired to determine if the RF coil was exactly over the heart. If not, the rabbit was moved and $^1$H image was then acquired to record the location and geometry of the heart for later comparison to the $^{23}$Na and $^{39}$K imaging. $^1$H imaging parameters were: imaging time 11 min; 4 phase encodes/cardiac cycle (gated to end-diastole); TE 2.5 ms; TR 50 ms; $N_{AVG}$=8; matrix size=128×64×64; voxel size=0.75×1.5×1.5 mm zero-filled during reconstruction to yield 0.75×0.75×0.75 mm resolution.

For $^{23}$Na imaging, the RF coil was then tuned to the $^{23}$Na frequency without moving the rabbit, and a 3D $^{23}$Na image was acquired at the same location. $^{23}$Na imaging parameters were: imaging time 20 min; 4 phases encodes/cardiac cycle (gated to end-diastole; TE 2.5 ms; TR 50 ms; $N_{AVG}$=32; matrix size=64×32×32; voxel size=1.5×3×3 mm zero-filled during reconstruction to yield 1.5×1.5×1.5 mm resolution.

For $^{39}$K imaging, $^1$H scouting was performed as described above. The RF coil was then tuned to the $^{39}$K frequency without moving the rabbit, and a 3D $^{39}$K image was acquired at the same location. Imaging parameters for $^{39}$K imaging were: imaging time 3 hours; 4 phase encodes/cardiac cycle (gated to end-diastole); TE 2.8 ms; TR 50 ms; $N_{AVG}$=512; matrix size=64×32×32; voxel size=4×8×8 mm zero-filled during reconstruction to yield 4×4×4 mm resolution.

What is claimed is:

1. A process of increasing the efficiency of $^{23}$Na magnetic resonance imaging of biological tissue, the process including the step of acquiring $^{23}$Na images using magnetic resonance imaging with a receiver bandwith equal to $R(N_{ro}/T^*_{2Na})$ where R is an integer from 1 to about 5 and $N_{ro}$ is the number of readout samples.

2. The process of claim 1 wherein R is from about 1 to about 3.

3. The process of claim 1 wherein R is from about 1 to about 2.

4. The process of claim 1 wherein the bandwidth is from about 500 Hz to about 10,000 Hz.

5. The process of claim 4 wherein the bandwidth is from about 1,000 Hz to about 5,000 Hz.

6. The process of claim 5 wherein the bandwidth is from about 2,500 Hz to about 5,000 Hz.

7. The process of claim 6 wherein the bandwidth is from about 2,500 Hz to about 3,000 Hz.

8. The process of claim 1 wherein $^{23}$Na images are acquired using a 1.5 T scanner.

9. The process of claim 8 wherein the images are acquired in from about 15 to about 60 minutes.

10. The process of claim 1 wherein $^{23}$Na images are acquired using a 3.0 T scanner.

11. The process of claim 10 wherein the images are acquired in from about 30 to about 45 minutes.

12. The process of claim 1 wherein $^{23}$Na images are acquired using a 4.0 T scanner.

13. The process of claim 12 wherein the images are acquired in about 30 minutes.

14. The process of claim 1 wherein the biological tissue is located in a living organism.

15. The process of claim 14 wherein the biological tissue is a human heart.

16. A process of increasing the efficiency of $^{39}$K magnetic resonance imaging of biological tissue, the process including the step of acquiring $^{39}$K images using magnetic resonance imaging with a receiver bandwidth equal or less than $R(N_{ro}/T^*_{2K})$ where R is an integer from 1 to about 5 and $N_{ro}$ is the number of readout samples.

17. The process of claim 16 wherein the bandwidth is from about 1,000 Hz to about 30,000 Hz.

18. The process of claim 17 wherein the bandwidth is about 8,000 Hz.

* * * * *

UNITED STATES PATENT AND TRADEMARK OFFICE
CERTIFICATE OF CORRECTION

PATENT NO.    : 5,910,112
DATED         : June 8, 1999
INVENTOR(S)   : Judd, Robert M.; Parrish, Todd B.; Lima, Joao A.C.; Kim, Raymond It is certified that error appears in the above-identified patent and that said Letters Patent is hereby corrected as shown below:

Title page,
Insert Item [75], Inventors, line 2, after "both of Ill":

-- Joao A.C. Lima, Timonium, MD;
Raymond Kim, Chicago, Ill. --

Signed and Sealed this

Twenty-ninth Day of January, 2002

Attest:

JAMES E. ROGAN
Attesting Officer        Director of the United States Patent and Trademark Office